United States Patent [19]
Rokita et al.

[11] Patent Number: 5,650,399
[45] Date of Patent: Jul. 22, 1997

[54] REACTIVE ANTHRAQUINONE DERIVATIVES AND CONJUGATES THEREOF

[75] Inventors: Steven E. Rokita, Port Jefferson; Hyunmin Kang, Stony Brook, both of N.Y.

[73] Assignee: The Research Foundation of State University of New York, Albany, N.Y.

[21] Appl. No.: 420,326

[22] Filed: Apr. 11, 1995

Related U.S. Application Data

[63] Continuation of Ser. No. 110,361, Aug. 23, 1993, abandoned.

[51] Int. Cl.$^6$ ............................. C07H 21/02; C07H 21/04
[52] U.S. Cl. ........................ 514/44; 536/24.5; 536/24.3; 552/265; 552/267
[58] Field of Search .......................... 514/44; 552/261, 552/262, 265, 267; 536/24.3, 24.5

[56] References Cited

U.S. PATENT DOCUMENTS

| | | | |
|---|---|---|---|
| 4,355,012 | 10/1982 | Renfrew et al. | 423/226 |
| 5,292,873 | 3/1994 | Rokita et al. | 536/24.3 |
| 5,296,350 | 3/1994 | Rokita et al. | 435/6 |

FOREIGN PATENT DOCUMENTS

PCT/WO85/ 02628  6/1985  WIPO .

OTHER PUBLICATIONS

Landegren et al., "DNA Diagnostics–Molecular Techniques and Automation", *Science*, 242, 229 (1988).

Miller et al., "Oligonucleotide Inhibitors of Gene Expression in Living Cells: New Opportunities in Drug Design", *Ann. Reports in Med. Chem.*, 23, 295 (1988).

Tolumé et al., "Antimessenger Oligodeoxyribonucleotides: An Alternative to Antisense RNA for Artificial Regulation of Gene Expression—A Review", *Gene*, 72, 51–58 (1988).

Stein et al., "Oligodeoxyribonucleotides as Inhibitors of Gene Expression: A Review", *Cancer Research*, 48, 2659–2668 (1988).

Barton, "Metals and DNA: Molecular Left–Handed Complements", *Science*, 233, 727–734 (1986).

Dervan, "Design of Sequence–Specific DNA–Binding Molecules", *Science*, 232, 464–471 (1986).

(List continued on next page.)

*Primary Examiner*—Kenneth R. Horlick
*Attorney, Agent, or Firm*—Hoffmann & Baron

[57] ABSTRACT

Anthraquinone derivatives are constructed for alkylation of target molecules. The anthraquinone derivative includes an anthraquinone ring system which has been modified by the addition of inducibly reactive substituents at positions on the ring system. The anthraquinone ring system can be selectively activated for alkylation of a target molecule. The substituents may be from 1 to 4 methyl groups, whereupon activation is achieved by a photochemical signal. In an additional alternative embodiment, the inducible reactive substituents may include both methyl groups and substituted methylene groups. In this embodiment, the activation of the anthraquinone derivative is achieved by photochemical and/or reductive signals. Alternatively, the substituents may be from 1 to 8 methyl groups modified to include a reactive group, whereupon activation is achieved by a chemical or enzymatic reductive signal. The anthraquinone derivatives of the invention may be used for non-specific modification of target molecules. Alternatively, the anthraquinone derivative may be further derivatized to permit specific modification of target molecules. The further derivatization of the anthraquinone includes attaching a probe to the anthraquinone ring system by way of a linking group. The probe is chosen to selectively localize to a target molecule, whereupon the anthraquinone derivative may be activated to react with and aklylate the target molecule. Also the process of employing such anthraquinone derivatives for use in vitro or in vivo for alkylating, specifically or non-specifically alkylating, target molecules.

32 Claims, 11 Drawing Sheets

OTHER PUBLICATIONS

Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985).

Agrawal et al., "Oligodeoxynucleoside Phosphoramidates and Phosphorothioates as Inhibitors of Human Immunodeficiency Virus", *Proc. Natl. Acad. Sci. USA*, 85, 7079–7083 (1988).

Iverson et al., "Nonenzymatic Sequence–Specific Cleavage of Single–Stranded DNA to Nucleotide Resolution. DNA Methyl Thiolether Probes", *J. Am. Chem. Soc.*, 109, 1241–1243 (1987).

Maher III et al., "Inhibition of DNA Binding Proteins by Oligonucleotide–Directed Triple Helix Formation", *Science*, 245, 725–730 (1989).

Griffin et al., "Recognition of Thymine–Adenine Base Pairs by Guanine in a Pyrimidine Triple Helix Motif", *Science*, 245, 967–971 (1989).

Strobel et al., "Site–Specific Cleavage of a Yeast Chromosome by Oligonucleotide–Directed Triple–Helix Formation", *Science*, 249, 73–75 (1990).

Symons, *Nucleic Acid Probes*, CRC Press, Inc., Boca Raton, Florida (1989).

Gamper et al., "Reverse Southern Hybridization", *Nucl. Acids Res.*, 14, 9943–9954 (1986).

Knorre et al., "Complementary–Addressed (Sequence Specific) Modification of Nucleic Acids", *Prog. Nucleic Acids Res. Mol. Biol.*, 32, 291–320 (1985).

Webb et al., "Sequence–Specific Crosslinking of Deoxyoligonucleotides via Hybridization–Triggered Alkylation", *J. Am Chem. Soc.*, 108, 2764–2765 (1986).

Meyer et al., "Efficient, Specific Crosslinking and Cleavage of DNA by Stable, Synthetic Complementary Oligonucleotides", *J. Am. Chem. Soc.*, 111, 8517–8519 (1989).

Van Houten et al., "Action Mechanism of ABC Excision Nuclease on a DNA Substrate Containing a Psoralen Crosslink at a Defined Position", *Proc. Natl. Acad. Sci. USA*, 83, 8077–8081 (1986).

Lee et al., "Interaction of Psoralen–Derivatized Oligodeoxyribonucleoside Methylphosphonates with Single–Stranded DNA", *Biochemistry*, 27, 3197–3203 (1988).

Chatterjee et al., "Inducible Alkylation of DNA Using an Oligonucleotide Quinone Conjugate", *J. Am. Chem. Soc.*, 112, 6397–6399 (1990).

Ramage et al, "Solid Phase Peptide Synthesis: Fluoride Ion Release of Peptide from the Resin", *Tet. Lett.*, 28, 4105–4108 (1987).

Mullen et al, "A New Fluoridolyzable Anchoring Linkage for Orthogonal Solid Phase Peptide Synthesis", *J. Org. Chem.*, 53, 5240–5248 (1988).

Trahanovsky et al., "Observation of Reactive o–Quinodimethanes by Flow NMR", *J. Am. Chem. Soc.*, 110, 6579–6581 (1988).

Angle et al, "p–Quinone Methide Initiated Cyclization Reactions", *J. Am. Chem. Soc.*, 111, 1136–1138 (1989).

Wahl et al., "Northern and Southern Blots", *Meth. Enzymol.*, 152, 572–573 (1987).

Higuchi et al., "DNA Typing from Single Hairs", *Nature*, 332, 543–546 (1988).

Conner et al., "Detection of Sickle Cell $\beta^s$–Globin Allele by Hybridization with Synthetic Oligonucleotides", *Proc. Natl. Acad. Sci. USA*, 80, 278–282 (1983).

Gebeyehu et al., "Novel Biotinylated Nucleotide–Analogs for Labelling and Colormetric Detection of DNA", *Nucl. Acids Res.*, 15, 4513–4534 (1987).

Jäger et al., "Oligonucleotide N–Alkyl–phosphoramides: Synthesis and Boindoing to Polynucleotides", *Biochemistry*, 27, 7237–7246 (1988).

Cocuzza, "Total Synthesis of 7–Iodo-2', 3'–Dideoxy–7–Deazpurine Nucleosides, Key Intermediates in the Preparation of Reagents for the Automated Sequencing of DNA", *Tet. Lett.*, 29, 4061–4064 (1988).

Hanna et al., "Synthesis and Characterization of 5–[(4–Azidophenacyl)thio]uridine 5'–Triphosphate, a Cleavable Photo–Cross Linking Nucleotide Analogue", *Biochemistry*, 28, 5814–5820 (1989).

Gibson et al., "Synthesis and Application of Derivatizable Oligonucleotides", *Nucl. Acids Res.*, 15, 6455–6467 (1987).

Nelson et al., "A New and Versatile Reagent for Incorporating Multiple Primary Aliphatic Amines Into Synthetic Oligonucleotides", *Nucl. Acids Res.*, 17, 7179–7186 (1989).

Maniatis et al., *Molecular Cloning, A Laboratory Manual*, Cold Spring Harbor Laboratory, Cold Spring Harbor, NY (1982).

Raval et al., "Condensation of Succinic Anhydride with Phenols" *J. Univ. Bombay*, 7, Pt. 3, 184–188 (1938); Chemical Abstracts, 33, 3779 (1939).

Dreyer et al., "Sequence–Specific Cleavage of Single–Stranded DNA: Oligodeoxynucleotide–EDTA–Fe(II)", *Proc. Natl. Acad. Sci. USA*, 82, 968–972 (1985).

Chu et al., "Nonenzymatic Sequence–Specific Cleavage of Single–Stranded DNA", *Proc. Natl. Acad. Sci. USA*, 82, 963–967 (1985).

Mack et al., "Design and Chemical Synthesis of a Sequence–Specific DNA–Cleaving Protein", *J. Am. Chem. Soc.*, 110, 7572–7574 (1988).

Remers, "Antineoplastic Agents", Ch. 8, *Wilson and Gisvold's Textbook of Organic Medicinal and Pharmaceutical Chemistry*, 9th Ed. Delgado et al., eds. 313–353, J.B. Lippincott Co., Philadelphia.

Goodchild, "Conjugates of Oligonucleotides and Modified Oligonucleotides: A Review of Their Synthesis and Properties", *Bioconjugate Chem.*, 1, 165–187 (1990).

Uhlmann et al., "Antisense Oligonucleotides: A New Therapeutic Principle", *Chem. Rev.*, 90, 543–584 (1990).

Nielsen, "Sequence–Selective DNA Recognition by Synthetic Ligands", *Bioconjugate Chem.*, 2, 1–12 (1991).

Englisch et al., "Chemically Modified Oligonucleotides as Probes and Inhibitors", *Angew. Chem. Int. Ed. Engl.*, 30, 613–629 (1991).

Brakel, ed., *Discoveries in Antisense Nucleic Acids*, Gulf Publishing Co., Houston (1989).

Praseuth et al., "Sequence–Specific Binding and Photocrosslinking of $\alpha$ and $\beta$ Oligodeoxynucleotides to the Major Groove of DNA via Triple–Helix Formation", *Proc. Natl. Acad. Sci. USA*, 85, 1349–1353 (1988).

Lin et al., "Hybridization Properties of Deoxyoligonucleotides Containing Anthraquinone Pseudonucleosides", *Nucl. Acids Res.*, 19, 3111–3114 (1991).

Takasugi et al., "Sequence–Specific Photo–Induced Cross–linking of the Two Strands of Double–helical DNA by a Psoralen Covalently Linked to a Triple Helix–forming Oligonucleotide", *Proc. Natl. Acad. Sci. USA*, 88, 5602–5606 (1991).

Maruyama et al., "A Novel Photocyclization Reaction of Lysine–Anthraquinone Molecules", *Chemistry Lett.*, 2165–2166 (1990).

Maruyama et al., "Site-selective Photocyclization of Acetylglycine–Anthraquinone Molecules", *Chemistry Lett.*, 1455–1456 (1991).

Gritsan et al., "Experimental and Theoretical Study of Photoenolization Mechanism for 1–Methylanthraquinone", *J. Am. Chem. Soc.*, 113, 9615–9620 (1991).

Rosenfeld et al., "Synthesis of an Isolable Quinodimethane", *J. Chem. Educ.*, 68, 691–692 (1991).

Tanimoto et al., "Spectroscopic Studies on the Intramolecular Hydrogen Abstraction Reactions of n–Alkyl Anthraquinone–2–carboxylates", *Bull. Chem. Soc. Jpn.*, 61, 3121–3127 (1988).

Mori et al., "Oligodeoxynucleotide Analogs with 5'–Linked Anthraquinone", *FEBS Lett.*, 249, 213–218 (1989).

Müller et al., "o–Bis–[Arylpropinoyl]–Benzol, IV. Mitteilung Übergangsmetallkomplexe und deren reaktives Verhalten", *Tet. Lett.*, 731–734 (1970).

Müller et al., "4,9–Dioxo–1,3–Diaryl–4,9–Dihydro–(Naphtho[2,3–c]–Furan). –Thiophen Und–Selenophen", *Tet. Lett.*, 735–736 (1970).

Müller et al., "Bis–[acetylenketone], IX. Mitteilung Übergangsmetallkomplexe und deren reaktives Verhalten", *Tet. Lett.*, 5271–5274 (1970).

Antonini et al., *J. Med. Chem.*, 25, 730–735 (1982).

Praseuth et al., *Biochemistry*, 27, 3031–3038 (1988).

Ratner, *Bio/Technology*, 7, 207 (1989).

Chatterjee et al., *J. Am. Chem. Soc.* 113, 5116–5117 (1991).

FIG-1 SCHEME 1

FIG-8 SCHEME 2

FIG-10 SCHEME 3

FIG-11 SCHEME 4

REACTIVE ANTHRAQUINONE DERIVATIVES AND CONJUGATES THEREOF

This is a continuation of application Ser. No. 08/110,361, filed on Aug. 23, 1993, abandoned.

BACKGROUND OF THE INVENTION

1. Field of the Invention

This invention relates to a process of using anthraquinone derivatives for the alkylation of target molecules, as well as the anthraquinone derivatives for the process. The anthraquinone derivatives useful for the process may be selectively activated by light irradiation and/or by enzymatic or chemical reduction.

2. Background of the Related Art

Currently prescribed chemotherapeutic agents acting at the level of DNA are often effective, but their therapeutic index is quite poor, limited by the lack of target specificity. An international research effort has been underway using a wide range of techniques to develop a gene specific drug—a "magic bullet" that is aimed not an individual organism or cell type, but a single gene sequence within a cell.

The technological advances allowing for facile DNA synthesis have produced innumerable protocols which rely on custom oligonucleotides, used as probes to screen for complementary sequences within plasmids, chromosomes and DNA libraries. See for example, Landegren et al., "DNA Diagnostics-Molecular Techniques and Automation", *Science*, 242, 229 (1988). The specificity of oligonucleotide hybridization has been utilized for "antisense" methods controlling selective expression of genes both in vivo and in vitro. For example, see Miller et al., "Oligonucleotide Inhibitors of Gene Expression in Living Cells: New Opportunities in Drug Design", *Ann. Reports in Med. Chem.*, 23, 295 (1988). Sequence recognition by the binding of probes most often depends on only the non-covalent forces of hydrogen bonding formed between complementary base pairs. Complexation of this type is quite sufficient for many applications, but covalent stabilization of duplex structures could simplify many of the current protocols and provide new opportunities for processing or modifying DNA in a sequence specific manner. Only recently introduced, the technique of oligonucleotide-directed irreversible DNA modification holds great potential as an in vitro tool for molecular biologists. See, for example, Dervan, "Design of Sequence-Specific DNA-Binding Molecules", *Science*, 232, 464–471 (1986); and Iverson et al., in "Nonenzymatic Sequence-Specific Cleavage of Single-Stranded DNA to Nucleotide Resolution. DNA Methyl Thioether Probes", *J. Am. Chem. Soc.*, 109, 1241–1243 (1987). Site specificity is enforced by the hybridization of the oligomer-reactant to its complement sequence prior to reagent action. Target selectivity can then be conferred, in theory, to most reactive compounds by attaching them to oligonucleotides. The required prehybridization step, however, generally limits this technique's applicability to accessible single strand polynucleotide targets or duplex probes when triple helical formation is possible. See Maher III et al., "Inhibition of DNA Binding Proteins by Oligonucleotide-Directed Triple Helix Formation", *Science*, 245, 725–730 (1989).

Recently, messenger RNA has become a viable target for inhibiting the expression of a desired gene in vivo. See, for example, Toulmé et al., "Antimessenger Oligodeoxyribonucleotides: An Alternative to Antisense RNA for Artificial Regulation of Gene Expression—A Review", *Gene*, 72, 51–58 (1988); and Stein et al., "Oligodeoxyribonucleotides as Inhibitors of Gene Expression: A Review", *Cancer Research*, 48, 2659–2668 (1988). Compounds created for this selective reaction have drawn from the advances in site specific modification of DNA. For example, see Barton, "Metals and DNA: Molecular Left-Handed Complements", *Science*, 233, 727–734 (1986), and Dervan, *Science*, 232 (1986) supra.

Use of such compounds also depends on the synthesis of metabolically stable oligonucleotides that can traverse cell membranes. For example, see Blake et al., "Hybridization Arrest of Globin Synthesis in Rabbit Reticulocyte Lysates and Cells by Oligodeoxyribonucleoside Methylphosphonates" *Biochemistry*, 24, 6139–6145 (1985). Also, see Agrawal et al., "Oligodeoxynucleoside Phosphoramidates and Phosphorothioates as Inhibitors of Human Immunodeficiency Virus" *Proc. Natl. Acad. Sci. USA*, 85, 7079–7083 (1988).

Although a large number of reactive appendages are available for related use in vitro, as reported by Iverson et al., *J. Am. Chem. Soc.*, 109 (1987) supra; and by Dervan, *Science*, 232 (1986) supra, it is possible that only a limited set of these might be useful for in vivo techniques. See Mori et al., in "Oligodeoxynucleotide Analogs with 5'-Linked Anthraquinone", *FEBS Letters*, 249,213–218 (1989), who reported the synthesis of a 5'-linked oligodeoxynucleotide in which a covalently attached group links the nucleotide to an anthraquinone molecule. The anthraquinone molecule was chosen for its potential radical-producing moiety, that does not necessarily require the presence of a metal ion or light activation. Such a molecule, however, is incapable of alkylating the target DNA. Also, it is likely that this anthraquinone moiety is not photochemically active in an alkylation reaction, due to the resonance structures within the ring system.

Wagner et al. have reported that methyl naphthoquinone sensitizes the selective oxidation of thymine, in "Photo-Oxidation of Thymine Sensitized by 2-Methyl-1,4-Naphthoquinone: Analysis of Products Including Three Novel Photo-Dimers", *Photochem. Photobiol.*, 40, 589–597, (1984).

An article by Antonini et al., entitled "2- and 6-Methyl-1,4-naphthoquinone Derivatives as Potential Bioreductive Alkylating Agents" *J. Med. Chem.*, 25, 730–735 (1982), describes a number of antineoplastic agents which possess both a quinone nucleus and a substituent that permits them to function as bioreductive alkylating agents. Antonini et al. reported the synthesis of a series of 2- and 6-methyl-1,4-naphthoquinone derivatives, and evaluated them for antitumor effects on mice bearing Sarcoma 180 ascites cells. These antitumor agents were thought to be activated by reduction to an alkylating species. Such reduction was believed to take place due to enzymes produced by the metabolic system of hypoxic tumor cells, functioning under low oxygen tension. Antonini et al. did not, however, describe or suggest either the use of anthraquinone derivatives or the delivery of the anthraquinone derivatives into cellular DNA by using a target specific probe. Nor did Antonini et al. describe the modification or use of such anthraquinones as UV activated alkylating agents. Additionally, while Antonini et al. insert the —$CH_2$—X group on carbon 6 of the benzene ring of the naphthaquinone ring system, they do not, however, suggest inserting the —$CH_2$—X group on the other positions of this benzene ring.

Two articles describe anthraquinone derivatives. Gritsan et al., in "Experimental and Theoretical Study of Photoenolization Mechanism for 1-Methylanthraquinone", *J. Am. Chem. Soc.*, 113, 9615–9620 (1991), describe photochemical activation of 1-methylanthraquinone. Gritsan et al. do not, however, describe alkylation reactions or methods of using 1-methylanthratquinone for alkylating target molecules. Nor does this publication describe linking 1-methylanthraquinone to moieties capable of associating, in a specific or selective manner, to target molecules.

Rosenfeld et al., in "Synthesis of an Isolable Quinodimethane", *J. Chem. Educ.*, 68, 691–692 (1991), describe a method for synthesizing a group of anthraquinone derivatives. The synthetic method includes a step of making 1,4-dimethylanthraquinone. Rosenfeld et al. do not describe activating the 1,4-dimethylanthraquinone or using 1,4-dimethylanthraquinone to alkylate target molecules.

Yabusaki et al., in PCT Published Application No. WO 85/02628 describe cross-linking agents for binding an oligonucleotide probe to a target DNA or RNA molecule. Three types of cross-linking agents are described, including "bifunctional photoreagents", "mixed chemical and biochemical bifunctional reagents" and "bifunctional chemical cross-linking molecules". The bifunctional photoreagents contain two photochemically reactive sites that bind covalently to the probe and to the target molecules. The mixed chemical and photochemical bifunctional reagent is bound non-photochemically to the probe molecule, followed by photochemical binding to the target molecule. Non-photochemical binding is described as a chemical reaction such as alkylation, condensation or addition. Bifunctional chemical cross-linking molecules are said to be activated either catalytically or by high temperature following hybridization.

Although Yabusaki et al. generally hypothesize the concept of a bifunctional photochemical reagent and a mixed chemical and photochemical reagent, there is no specific description of these molecules. All of the reagents they describe are well known photochemical reagents. These compounds include the psoralen derivatives, including furocoumarins, the benzodipyrone derivatives, and the bisazide derivatives. None of these molecules, however, work on the basis of reductive activation. In addition, these compounds are not very specific in vivo. It would be difficult or nearly impossible to photoactivate these reagents in vivo. These reagents, especially the psoralen derivatives are toxic, causing severe burning of the organism after exposure to sunlight. Finally, the covalent crosslinks formed by psoralens are not permanent, rather, they are degraded by further UV irradiation.

Several recent articles reported the use of psoralen crosslinks DNA substrates, see Van Houten et al., in "Action Mechanism of ABC Excision Nuclease on a DNA Substrate Containing a Psoralen Crosslink at a Defined Position", *Proc. Natl. Acad. Sci. USA*, 83, 8077–8081 (1986); Lee et al., in "Interaction of Psoralen-Derivatized Oligodeoxyribonucleoside Methyl-phosphonates with Single-Stranded DNA", *Biochemistry*, 27, 3197–3203 (1988); and Takasugi et al., "Sequence-specific Photo-induced Cross-linking of the Two Strands of Double-helical DNA by a Psoralen Covalently Linked to a Triple Helix-forming Oligonucleotide", *Proc. Natl. Acad. Sci. USA*, 88, 5602–5606 (1991). Each of these articles report covalent cross-linking between the DNA molecule and a complementary oligomer that contains a psoralen derivative. The covalent binding of the psoralen derivative to the DNA molecule was in each case activated by UV irradiation. Accordingly, just like the Yabusaki patent application, none of these references describe the chemically activated covalent binding agent which may be used in vivo. Additionally, as discussed above, the covalent crosslinks formed by psoralens are not permanent, being degraded by UV irradiation.

The techniques of Northern and Southern blotting are two of the most powerful and frequently used procedures in molecular biology. See Wall et al., "Northern and Southern Blots", *Meth. Enzymol.*, 152, 572–573 (1987). Yet the necessary manipulations are time consuming and are not likely to be automated under current technology. Often the polynucleotide (RNA, DNA) under analysis must first be fractionated by size, transferred onto a solid support and then treated through a series of steps to ensure only specific binding of a probe. Detection of the hybridized products usually depends on radiolabelling, heavy metal derivatization, or antibody complexation. The methods of blotting have been a staple of basic research, and now also serve in an ever increasing number of commercial kits used to diagnose genetic, malignant, and infectious diseases. See Landegren et al., *Science*, 242, (1988) supra. Related advances have also allowed these processes to aid in forensic science, see Higuchi et al., "DNA Typing from Single Hairs", *Nature*, 332, 543–546 (1988); and the Human Genome Project, see Conner et al., "Detection of Sickle Cell $\beta^s$-Globin Allele by Hybridization with Synthetic Oligonucleotides", *Proc. Natl. Acad. Sci. USA*, 80,278–282 (1983).

Psoralens have been used to randomly crosslink duplex DNA during hybridization in order to facilitate Southern Blotting procedures. This new test is referred to as Reverse Southern blotting. For example, see Gamper et al., "Reverse Southern Hybridization", *Nucl. Acids Res.*, 24., 9943 (1986). Other biochemical and reduction activated reagents are needed to replace or complement psoralens for sequence detection and to provide an alternate set of conditions for duplex stabilization.

Accordingly, none of the related art describes or suggests using UV and/or visible light ("UV/VIS") activation with an anthraquinone derivative in order to permanently alkylate a biological molecule such as DNA. Nor does the related art describe reductive activation of anthraquinone derivatives for the alkylation of biological molecules such as DNA.

Therefore, it is a purpose of the present invention to provide a new class of reductively and/or photochemically activated alkylating compounds which form a permanent covalent crosslink. Another goal of the present invention is to provide a alkylating probe, activated photochemically or by reduction, which can be used in vivo.

A further purpose of the present invention is to provide a new class of photochemical and reduction activated Reverse Southern blotting reagents for conjugating and permanently crosslinking target nucleic acid sequences and facilitating blotting procedures, sequence detection and strand scission.

SUMMARY OF THE INVENTION

These and other purposes and goals are achieved by the present invention which provides a process and composition for selectively and permanently alkylating a target molecule. The process includes a step of providing an alkylating agent, namely an anthraquinone derivative (AQ derivative), capable of alkylating a target molecule in response to a chemical or photochemical trigger. The anthraquinone derivative is preferably linked to a probe or recognition factor capable of associating to a target molecule. The probe, such as an oligonucleotide, may be capable of recognizing a specific predetermined association site on the target molecule, such as a specific nucleotide sequence of a nucleic acid highly complementary to the probe. The probe may also be chosen, however, to localize non-specifically or relatively non-specifically (i.e., selectively) to a target molecule or class of such target molecules. Alternatively, the anthraquinone derivative may non-specifically localize to the target molecule, e.g., by intercalation into duplex DNA.

The process further includes a step of introducing the anthraquinone derivative into a system containing a target molecule. The system may be either an in vivo system or an in vitro system.

The process also includes a step of activating the anthraquinone derivative to cause the alkylation of a target molecule. Depending upon the specific structure of the anthraquinone derivative employed in the process, the activating step may include photochemical activation by light irradation. Alternatively, the activating step may include a reductive chemical or enzymatic signal. In addition the activating step may include a combined use of photochemical and reductive activation procedures.

The preferred compounds useful according to the process of the invention include targeted anthraquinone derivatives having the general formula:

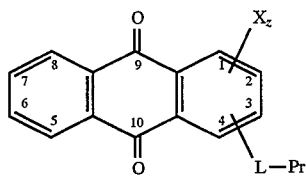

wherein X is an inducible reactive moiety, such as a methyl group or a —CH$_2$—Y group; z is an integer from 1 to 7; L is a linking group for attachment to a probe, which may be positioned at any free carbon atom on the ring system; and Pr is a probe (recognition factor) for associating to a target molecule.

In this embodiment, when X is a methyl group, z is an integer from 1 to 4, i.e., from 1 to 4 methyl groups may be present, and the methyl groups are attached to any of carbon atoms 1, 4, 5, and 8 of the anthraquinone ring system. In this embodiment, the anthraquinone alkylating agent is activated by light irradiation, once the alkylating agent has been allowed to associate with the target molecule. The preferred radiation for the photochemically activated alkylating agents of the invention is ultraviolet light, most preferably of a wavelength longer than 320 nm, but shorter than 420 nm.

Alternatively, in another embodiment, the X group is an inducible reactive moiety having the general formula —CH$_2$—Y, wherein the methylene group is attached to the anthraquinone ring system, and wherein Y is a displaceable reactive group. Examples of displaceable Y groups include —Br, —Cl, —F, —I, —OAc, —OH, —OSO$_2$CH$_3$, —OSO$_2$C$_6$H$_4$CH$_3$, —OCH$_2$CH$_3$, —OCONHCH$_3$, and —OCONHCH$_2$CH$_2$Cl. In this embodiment, the alkylating agent is activated by a reductive signal. The reductive signal may occur naturally within the cell, for example, through an enzyme mediated pathway, or may be introduced into the local environment of the target molecule. When X is an inducible reactive —CH$_2$—Y moiety, z is an integer from 1 to 7, and each —CH$_2$—Y group is attached at one of the eight available positions on carbon atoms 1–8 of the anthraquinone ring system. At least one of carbon atoms 1–8 in this embodiment is attached to an L-Pr group.

The linking group L is made up of a chain —R$_1$—R$_2$—R$_3$—. Generally the R$_1$ group may include a group for linking to the anthraquinone derivative, such as —CH$_2$—CH$_2$—CO—NH—, —NH—, —S—, —O— or —CH$_2$—. The R$_2$ group can include any spacer group that can link R$_1$ and R$_3$ such as an alkyl chain. Examples of R$_2$ spacers include alkyl chains, preferably chains from 2 to 10 carbon atoms in length, more preferably hexyl groups; and alkyl piperazinyl groups, preferably ethyl piperazinyl groups. The R$_3$ group is any group that can link R$_2$ to a modified oligonucleotide or other probe Pr. Examples of R$_3$ groups include NH, S, —Nh—, —S—, —Cl$_2$—, —CH$_2$—, —O— and COOH—CO—. Preferred L linking groups include alkanol amines and alcohol piperazines, most preferably ethanolamine, hexanolamine and 1-(2-hydroxyethyl) piperazine.

The probe Pr includes any localizing moiety, such as an oligonucleotide, oligopeptide, or other molecule that preferentially localizes to a target molecule, including DNA, RNA, or protein. The preferred probe is an oligonucleotide. For in vivo use the oligonucleotide is preferably modified according to methods known to those persons skilled in the art.

A more preferred compound useful according to the process of the invention has the following structure:

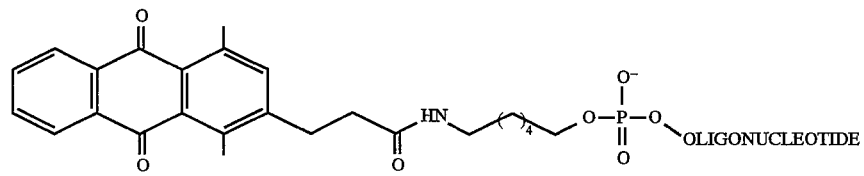

In another alternative embodiment, the anthraquinone compounds of the invention have the general molecular formula:

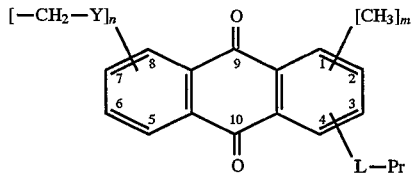

wherein m is an integer from 1 to 4 and n is an integer from 1 to 6, such that m+n≦7. That is, the compounds of the invention may include from 1 to 4 methyl groups and simultaneously include from 1 to 6 —CH$_2$—Y groups, wherein Y is a displaceable moiety as defined above. The sum total of the attached methyl and —CH$_2$—Y groups may not exceed 7, which corresponds to the number of available carbon atoms on the anthraquinone ring system given the attachment of the L-Pr moiety at one such carbon atom. The methyl groups may be attached at any of carbon atoms 1, 4, 5, 8 of the anthraquinone ring system. The —CH$_2$—Y groups may be attached at any of carbon atoms 1–8 of the ring system. Because the compounds of the invention in this embodiment possess inducible reactive moieties which are activatable by a light irradiation (—CH$_3$) and inducible reactive moieties which are activatable by a reductive signal (—CH$_2$—Y) the compounds are "bifunctional".

In an alternative embodiment, the anthraquinone derivatives useful according to the process of the invention have the general molecular formula:

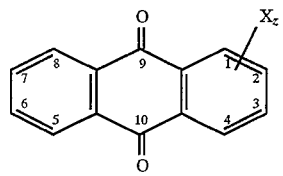

In this embodiment X is an inducible reactive moiety as described above for the targeted anthraquinone derivatives useful according to the process of the invention. In once aspect, therefore, X may be a methyl group and z is an integer from 1 to 4. From 1 to 4 methyl groups may be attached at carbon atoms 1, 4, 5, 8 of the anthraquinone ring system. In another aspect of this embodiment, the X group may have the general molecular formula —CH$_2$—Y, wherein Y is a displaceable moiety as defined above. In this aspect z is an integer from 1 to 8, and the —CH$_2$—Y groups may be attached at any of carbon atoms 1–8 of the anthraquinone ring system.

In a further embodiment, anthraquinone compounds useful according to the process of the invention are bifunctional compounds, as defined above, having the general molecular formula:

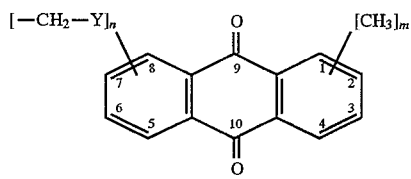

In this embodiment, m is an integer from 1 to 4 and n is an integer from 1 to 7, such that m+n≦8. From 1 to 4 methyl groups may be attached at any of carbon atoms 1, 4, 5, 8 of the anthraquinone ring system. Also from 1 to 7 —CH$_2$—Y groups may be attached at any of carbon atoms 1 to 8 of the anthraquinone ring system.

For a better understanding of the present invention, reference is made to the following description made in conjunction with the figures, the scope of which is defined in the claims.

DETAILED DESCRIPTION OF THE INVENTION

Figure 1:
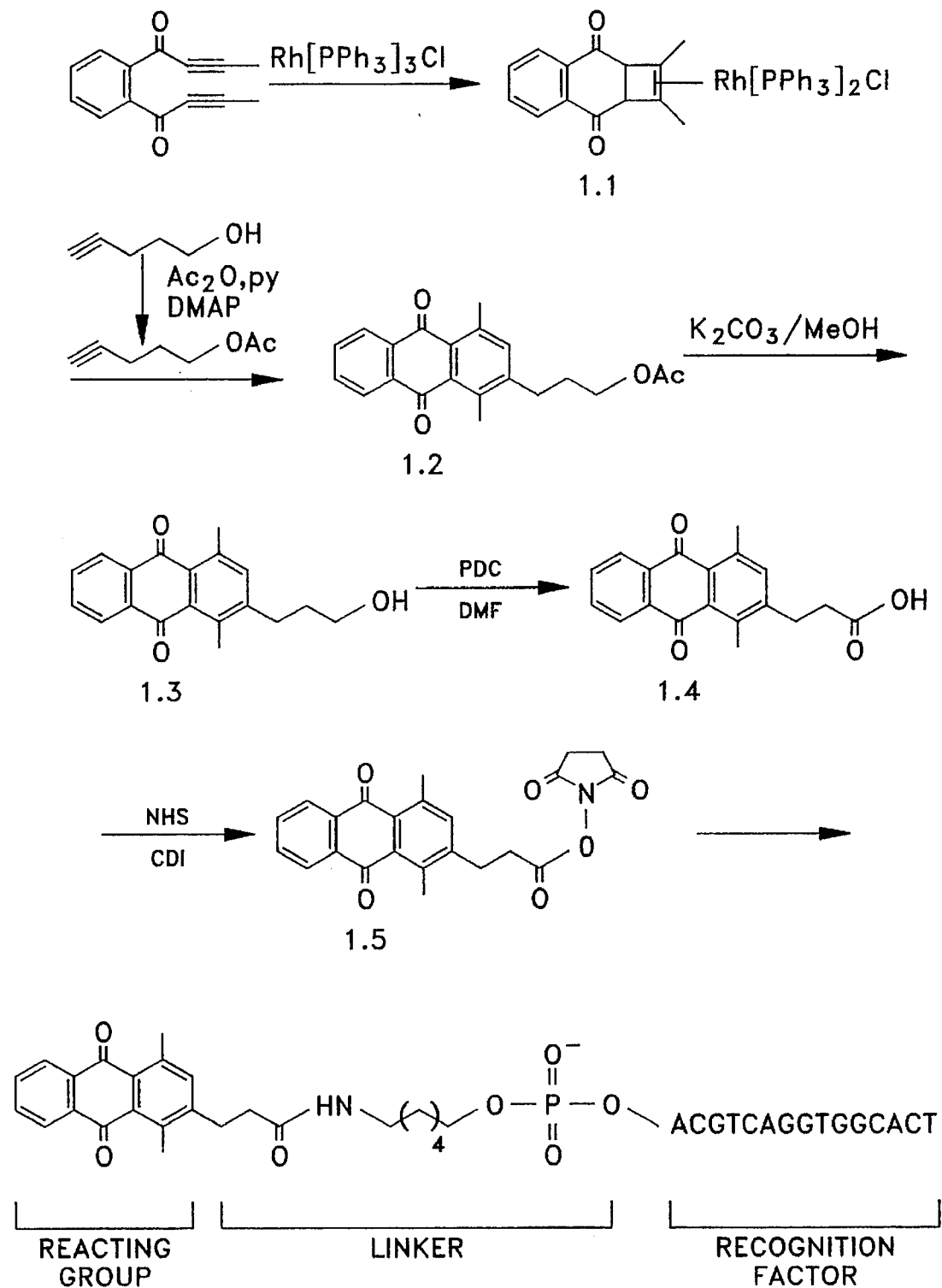
FIG. 1 illustrates a reaction sequence for synthesis of a targeted anthraquinone derivative of the invention. (Scheme 1).

The present invention provides a process and composition for selectively and permanently alkylating a target molecule. The process includes a step of providing an alkylating agent, namely an anthraquinone derivative (AQ derivative), capable of alkylating a target molecule in response to a chemical or photochemical trigger. The anthraquinone derivative is preferably linked to a probe or recognition factor capable of associating to a target molecule. The probe, such as an oligonucleotide, may be capable of recognizing a specific predetermined association site on the target molecule, such as a specific nucleotide sequence of a nucleic acid highly complementary to the probe. The probe may also be chosen, however, to localize non-specifically or relatively non-specifically (i.e., selectively) to a target molecule or class of such target molecules. Alternatively, the anthraquinone derivative may non-specifically localize to the target molecule, e.g., by intercalation into duplex DNA. It is believed that the anthraquinone derivatives useful according to the process of the invention neither impede the cellular uptake of appropriately modified nucleotides nor react indiscriminately with DNA.

The process further includes a step of introducing the anthraquinone derivative into a system containing a target molecule. The system may be either an in vivo system or an in vitro system.

The process also includes a step of activating the anthraquinone derivative to cause the alkylation of a target molecule. Depending upon the specific structure of the anthraquinone derivative employed in the process, the activating step may include photochemical activation by light irradation. Alternatively, the activating step may include a reductive chemical or enzymatic signal. In addition the activating step may include a combined use of photochemical and reductive activation procedures.

The preferred compounds useful according to the process of the invention include targeted anthraquinone derivatives having the general formula:

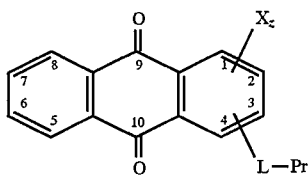

wherein X is an inducible reactive moiety, such as a methyl group or a —$CH_2$—Y group; z is an integer from 1 to 7; L is a linking group for attachment to a probe, which may be positioned at any free carbon atom on the ring system; and Pr is a probe (recognition factor) for associating to a target molecule.

In this embodiment, when X is a methyl group, z is an integer from 1 to 4, i.e., from i to 4 methyl groups may be present, and the methyl groups are attached to any of carbon atoms 1, 4, 5, and 8 of the anthraquinone ring system. In this embodiment, the anthraquinone alkylating agent is activated by light irradiation, once the alkylating agent has been allowed to associate with the target molecule. The preferred radiation for the photochemically activated alkylating agents of the invention is ultraviolet light, most preferably of a wavelength longer than 320 nm, but shorter than 420 nm.

Alternatively, in another embodiment, the X group is an inducible reactive moiety having the general formula —$CH_2$—Y, wherein the methylene group is attached to the anthraquinone ring system, and wherein Y is a displaceable reactive group. Examples of displaceable Y groups include —Br, —Cl, —F, —I, —OAc, —OH, —$OSO_2CH_3$, —$OSO_2C_6H_4CH_3$, —$OCH_2CH_3$, —$OCONHCH_3$, and —$OCONHCH_2CH_2Cl$. In this embodiment, the alkylating agent is activated by a reductive signal. The reductive signal may occur naturally within the cell, for example, through an enzyme mediated pathway, or may be introduced into the local environment of the target molecule. When X is an inducible reactive —$CH_2$—Y moiety, z is an integer from 1 to 7, and the each —$CH_2$—Y group is attached at one of the eight available positions on carbon atoms 1–8 of the anthraquinone ring system. At least one of carbon atoms 1–8 in this embodiment is attached to an L-Pr group.

The linking group L is made up of a chain —$R_1$—$R_2$—$R_3$—. Generally the $R_1$ group may include a group for linking to the anthraquinone derivative, such as —$CH_2$—$CH_2$—CO—NH—, —NH—, —S—, —O— or —$CH_2$—. The $R_2$ group can include any spacer group that can link $R_1$ and $R_3$ such as an alkyl chain. Examples of $R_2$ spacers include alkyl chains, preferably chains from 2 to 10 carbon atoms in length, more preferably hexyl groups; and alkyl piperazinyl groups, preferably ethylpiperazinyl groups. The $R_3$ group is any group that can link $R_2$ to a modified oligonucleotide or other probe Pr. Examples of $R_3$ groups include NH, S, —Nh—, —S—, —$CH_2$—, —O—, —COO— and COO. Preferred L linking groups include alkanol amines and alcohol piperazines, most preferably ethanolamine, hexanolamine and 1-(2-hydroxyethyl) piperazine.

The probe Pr includes any localizing moiety, such as an oligonucleotide, oligopeptide, or other molecule that preferentially localizes to a target molecule, including DNA, RNA, or protein. The preferred probe is an oligonucleotide. For in vivo use the oligonucleotide is preferably modified according to methods known to those persons skilled in the art.

A more preferred compound useful according to the process of the invention has the following structure:

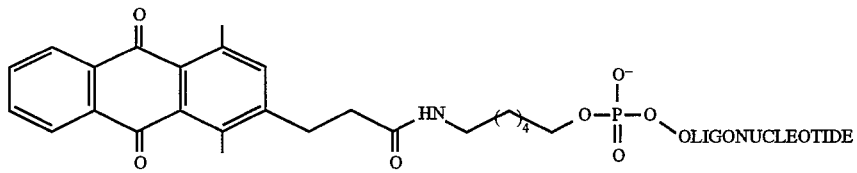

In another alternative embodiment, the anthraquinone compounds of the invention have the general molecular formula:

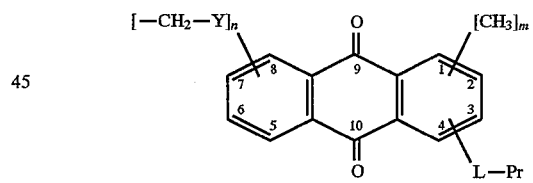

wherein m is an integer from 1 to 4 and n is an integer from 1 to 6, such that m+n≦7. That is, the compounds of the invention may include from 1 to 4 methyl groups and simultaneously include from 1 to 6 —$CH_2$—Y groups, wherein Y is a displaceable moiety as defined above. The sum total of the attached methyl and X groups may not exceed 7, which corresponds to the number of available carbon atoms on the anthraquinone ring system given the attachment of the L-Pr moiety at one such carbon atom. The methyl groups may be attached at any of carbon atoms 1, 4, 5, 8 of the anthraquinone ring system. The —$CH_2$—Y groups may be attached at any of carbon atoms 1–8 of the ring system. Because the compounds of the invention in this embodiment possess inducible reactive moieties which are activatable by a light irradiation (—$CH_3$) and inducible reactive moieties which are activatable by a reductive signal (—$CH_2$—Y) the compounds are "bifunctional".

In an alternative embodiment, the anthraquinone derivatives useful according to the process of the invention have the general molecular formula:

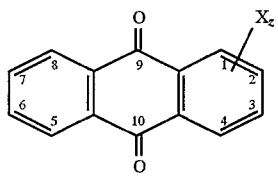

In this embodiment X is an Inducible reactive moiety as according to the process of the invention. In one aspect, therefore, X may be a methyl group and z is an integer from 1 to 4. From 1 to 4 methyl groups may be attached at carbon atoms 1, 4, 5, 8 of the anthraquinone ring system. In another aspect of this embodiment, the X group may have the general molecular formula —$CH_2$—Y, wherein Y is a displaceable moiety as defined above. In this aspect z is an integer from 1 to 8, and the —$CH_2$— Y groups may be attached at any of carbon atoms 1–8 of the anthraquinone ring system.

In a further embodiment, anthraquinone compounds useful according to the process of the invention are bifunctional compounds, as defined above, having the general molecular formula:

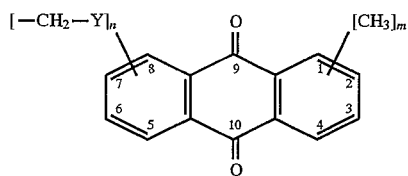

In this embodiment, m is an integer from 1 to 4 and n is an integer from 1 to 7, such that m+n≦8. From 1 to 4 methyl groups may be attached at any of carbon atoms 1, 4, 5, 8 of the anthraquinone ring system. Also from 1 to 7 —$CH_2$—Y groups may be attached at any of carbon atoms 1 to 8 of the anthraquinone ring system.

When the probe Pr is an oligonucleotide, whether unmodified DNA or DNA modified for in vivo use, the oligonucleotide may be linked to $R_3$ of the linking group L by the 5' or the 3' terminus of the oligonucleotide strand. Alternatively, the oligonucleotide probe may be linked to $R_3$ at any intermediate base in the oligonucleotide. For in vivo use, the oligonucleotide is preferably modified to increase the oligonucleotide's effectiveness. For example, it may be desirable to increase the oligonucleotide's resistance to in vivo degradation and to increase its capacity to diffuse or to be transported into cells. Methods of modifying oligonucleotides for use in vivo are well known to those persons skilled in the art. Such methods include incorporating into the oligonucleotide one or more modified bases, or by preparing a synthetic nucleic acid structure having a modified phosphoribose backbone. See, for example, Uhlmann et al., "Antisense Oligonucleotides: A New Therapeutic Principle", Chemical Reviews, 90,543–584 (1990), and Goodchild, "Conjugates of Oligonucleotides and Modified Oligonucleotides: A Review of Their Synthesis and Properties", Bioconjugate Chemistry, 1, 165–187 (1990).

In these embodiments, the linker group L may be selected to attach to a backbone of an oligonucleotide, or the linker group L may be modified to include a phosphate moiety which renders the targeted anthraquinone derivative a pseudonucleoside suitable for incorporation at any position in a synthetic oligonucleotide, that can be prepared by one of many well known standard methods, such as solid phase phosphoramidite protocols. Methods of preparing such linker-probe (L-Pr) complexes are well-known to those skilled in the art and have been described in various publications. Some representative publications include the following:

1. Brakel, Ed., "Discoveries in Antisense Nucleic Acids", Gulf Publishing Company, Houston (1989).

2. Englisch et al., "Chemically Modified Oligonucleotides as Probes and Inhibitors", Angewandte Chemie Int. Ed., 30, 613–722 (1991).

3. Nielsen, "Sequence-Selective DNA Recognition by Synthetic Ligands", Bioconjugate Chemistry, 1, 1–12 (1991).

4. Uhlmann et al., "Antisense Oligonucleotides: A New Therapeutic Principle", Chemical Reviews, 90, 543–584 (1990).

5. Goodchild, "Conjugates of Oligonucleotides and Modified Oligonucleotides: A Review of Their Synthesis and Properties", Bioconjugate Chemistry, 1, 165–187 (1990).

6. Gebeyehu et al., "Novel Biotinylated Nucleotide-Analogs for Labelling and Colorimetric Detection of DNA", Nucl. Acids Res., 55, 4513–4534 (1987).

7. Jäger et al., "Oligonucleotide N-Alkylphosphotamides: Synthesis and Binding to Polynucleotides", Biochemistry, 27, 7237–7246 (1988).

8. Cocuzza, "Total Synthesis of 7-Iodo-2',3'-Dideoxy-7-Deazapurine Nucleosides, Key Intermediates in the Preparation of Reagents for the Automated Sequencing of DNA", Tet. Letts., 29, 4061–4064 (1988).

9. Hanna et al., "Synthesis and Characterization of 5-[(4-Azidophenacyl)thio]uridine 5'-Triphosphate, a Cleavable Photo-Cross-Linking Nucleotide Analogue", Biochemistry, 28, 5814–5820 (1989).

10. Gibson et al., "Synthesis and Application of Derivatizable Oligonucleotides", Nucl. Acids Res., 15, 6455–6467 (1987).

11. Nelson et al., "A New and Versatile Reagent for Incorporating Multiple Primary Aliphatic Amines Into Synthetic Oligonucleotides", Nucl. Acids Res., 17, 7179–7186, (1989).

The present invention also describes a process for selectively alkylating a target molecule. A great number of useful clinical and laboratory applications are known, in which this process may be applied. For example, the compounds and processes of the invention may be integrated into applications such as those described in PCT published Application No. WO 85/02628 to Yabusaki et al., and in the article by Antonini et al., J. Med. Chem., 25, 730–735 (1982). The anthraquinone derivatives of the invention are also potentially useful in the process of Reverse Southern Blotting, described generally in the Background of the Related Art, supra.

Generally, the process for employing a targeted anthraquinone derivative according to the invention is carried out by initially providing a probe or recognition factor for recognizing a predetermined association site on a target molecule. For certain purposes, the probe may include a strand of unmodified DNA or DNA modified for in vivo use. See, for example, Praseuth et al., "Sequence-Specific Bonding and Photocrosslinking of α and β Oligodeoxynucleotides to the Major Groove of DNA via Triple-Helix Formation", Proc. Natl. Acad. Sci. USA, 85, 1349–1353

(1988). Alternatively, it may include any other molecule which can localize the probe to a target molecule. For example, Dervan et al., "Design of Sequence-Specific DNA-Binding Molecules", *Science*, 232, 464–471 (1986) describes a variety of well known natural and synthetic compounds that bind DNA in a sequence-specific manner and which comprise a series of subunits linked by peptide bonds. Among these compounds potentially useful as probes in accordance with the invention is actinomycin, which acts as an intercalator by means of a phenoxazone moiety, and binds 4 base pairs above and below the intercalation site by means of identical cyclic pentapeptide lactones. Actinomycin exhibits a preference for 5'-NGCN-3' sequences. This publication also describes alternative modes of peptide binding to double-helical DNA, such as the minor groove sequence-specific binding exhibited by distamycin, a crescent-shaped tripeptide containing three N-methylpyrrole carboxamides linked by peptide bonds. Comparable sequence-selective binding is shown for oligopeptides having up to 7 amide linkages. Synthetic sequence specific probes are known which utilize a combination of intercalation and minor groove binding as a means for identifying double-helical DNA sequences up to 10 base pairs in length. Accordingly, the Dervan article illustrates that a large variety of probes potentially useful for the invention are known in the art, including intercalating moieties, peptides of variable length and structure, or even combinations of various localizing molecules.

Various methods are known for linking anthraquinone molecules to amino acids via linking groups containing alkyl chains. Among these are Maruyama et al., "Site-Selective Photocyclization of Acetylglycine-Anthraquinone Molecules", *Chem. Letts.*, 1455–1456 (1991), and Maruyama et al., "A Novel Photocyclization Reaction of Lysine-Anthraquinone Molecules", *Chem. Letts.*, 2165–2166 (1990).

The Dervan publication also provides a description of the binding of organometallo complexes to DNA. This type of localizing molecule is further described in a review by Barton entitled "Metals and DNA: Molecular Left-Handed Complements", *Science*, 233, 727–734 (1986). The Barton publication describes chiral metal complexes capable of various structural interactions with DNA including stereoselective intercalation, groove binding, and direct coordination. Such metal complexes may be useful as probes in accordance with the present invention.

It is preferred that neither the probe Pr nor the linker group L, introduce significant steric hindrance to the localization and/or intercalation of the AQ derivative to the target molecule. In particular, Lin et al., "Hybridization Properties of Deoxyoligonucleotides Containing Anthraquinone Pseudonucleosides", *Nucleic Acids Res.*, 19, 3111–3114 (1991), have shown that various linker groups may be used to integrate anthraquinone into oligonucleotides while introducing little or no instability into the association of the complex to complementary DNA. For example, no pronounced effect on stability is caused by the length of the linker arm. Lin et al. show that AQ pseudonucleoside complexes, wherein the AQ is linked to either a 2-(N,N-dihexanolamino) group or a 2-(N,N-diethanolamino) group, bind stably to DNA. This effect is independent of whether the AQ pseudonucleoside is linked to the oligonucleotide at the 5' or 3' end. In addition, the AQ moiety exhibits a stabilizing effect on the association of the oligonucleotide even when positioned at an intermediate position in the oligonucleotide.

Similarly, Mori et al., "Oligonucleotide Analogs with 5'-Linked Anthraquinone", *FEBS Letts.*, 249, 213–218 (1989), show that anthraquinone may be linked to oligonucleotides by a hexamethylene or 2-hydroxyethylpiperazinyl linker group without interfering with the intercalation of AQ into DNA or destabilizing the duplex formed between the oligonucleotide and the complementary DNA. The Lin et al. and Mori et al. publications show that a wide variety of linker-probe (L-Pr) configurations may potentially be employed without compromising the structural interactions between the targeted AQ derivative of the invention and the target nucleic acids. See also Examples 13 and 14 below.

The process of the invention is preferably carried out by providing an AQ derivative which is modified for linking to the probe molecule. The Pr molecule is then linked to the AQ derivative to create a targeted alkylating agent. The process then includes a step of introducing the targeted alkylating agent into a system containing a target molecule. The Pr molecule associates with the target molecule, localizing the linked AQ derivative near the target molecule. Crosslinking or covalent bonding is then initiated by activating the targeted alkylating agent either by a reductive signal or light irradiation, or a sequential or simultaneous combination thereof, depending on the structure of the AQ derivative being employed. A covalent bond is then formed between the AQ derivative and the target, proximal to the association site of the Pr molecule with the target molecule. The process proceeds in a similar fashion when an anthraquinone derivative is used which is not linked to a probe, but which selectively or non-specifically associates to a target molecule.

The AQ derivatives of the invention include at least one inducible reactive substituent groups or "arms" attached to the AQ ring system, preferably methyl ($CH_3$) groups or substituted methyl groups. When the AQ moiety includes two methyl group arms, the step of activating alkylation and covalent bonding between the associated probe and target molecule is carried out by light irradiation.

If the arms attached to the AQ ring system are inducible reactive groups which include displaceable moieties, such as bromomethyl groups or any of the other substituted methylene groups ($—CH_2—Y$) described supra, activation is carried out by a reductive signal, such as reduction by an enzyme in a system containing the target molecule; or, by the introduction of other reducing agents, such as sodium borohydride, dithionite, sodium cyanoborohydride, and thiols, in vitro.

Preferably, if reductive activation is desired, an adapting step of adding a carboxyl linking group to the anthraquinone compound may be followed by a bromination step which replaces one of the hydrogen atoms on the methyl arm with a bromine atom. If displaceable groups other than bromine are desired, the bromination step may be followed by a substitution of the bromine with other displaceable groups such as Cl, F, I, -OAc, -OH, $—OSO_2CH_3$, $—OSO_2C_6H_4CH_3$, $—OCH_2CH_3$, $—OCONHCH_3$, and $—OCONHCH_2CH_2Cl$.

The process of this invention employing reductive activation of the AQ derivative may be carried out in vivo, and the activation may be triggered by an enzyme catalyzed reduction within the organism that contains the target molecule. Such activation is described in detail in commonly assigned U.S. patent application Ser. No. 07/442,947, with regard to naphthaquinones, the disclosure of which is incorporated by reference herein.

If in vivo use is desired, then suitably modified probes that are capable of traversing cell membranes are prepared, for example, as described by Blake et al., "Hybridization Arrest of Globin Synthesis in Rabbit Reticulocyte Lysates and Cells by Oligodeoxyribonucleoside Methyl-phosphonates", *Biochemistry*, 24, 6139–6145 (1985); and, by Agrawal et al., "Oligodeoxynucleoside Phosphoramidates and Phosphorothioates as Inhibitors of Human Immunodeficiency Virus", *Proc. Natl. Acad. Sci. USA*, 85, 7079–7083 (1988). These probes are then attached to activated esters. Alternatively, a reductive signal may be selectively introduced in order to trigger alkylation and crosslinking.

For example, in mice attacked by cancer cells, as reported by Antonini et al., (1982), supra, hypoxic tumor cells create a reducing environment for enzymes which in turn cause reduction and thereby selectively trigger similar naphthoquinone derivatives having inducible reactive groups. Antonini et al., however, did not target their naphthoquinone derivative by using a probe of any kind.

The process of this invention can, of course, be carried out in vitro using either reductive or photochemical activation. In fact, photochemical activation may even be used in vivo by introducing a fiber optic filament, capable of transmitting ultraviolet or visible light, into the organism through a needle or catheter for site specific activation of crosslinking.

Nucleic acids have recently begun to be considered as therapeutic targets for inhibiting the expression of specific genes in vivo. While some compounds such as bleomycin, have demonstrated limited sequence specificity it appears likely that only an antisense or triplex approach will provide absolute specificity. Few reagents or appendages are currently available to combine with this new approach for creating a controlled and covalent activity in vivo. In a continuing effort to develop such a species, the inventors have examined a series of compounds as inducible precursors to highly reactive quinone methide intermediates. For example, a 5-methylnaphthoquinone derivative was used to alkylate DNA under irradiation of λ>340 nm, but the general chemical and photochemical instability of this quinone limited the final yields to no greater than 20%. The related photochemistry of 1-methylanthraquinone (See Gritsan et al., "Experimental and Theoretical Study of Photoenolization Mechanism for 1-Methylanthraquinone", *J. Am. Chem. Soc.*, 113, 9615–9620 (1991)) has now been incorporated into more highly stable and efficient alkylating agents of DNA through the synthesis of various AQ derivatives, including 1,4-dimethylanthraquinone (hereinafter abbreviated $Me_2AQ$). Most importantly, these compounds may ultimately serve to alkylate two or more adjacent strands of DNA and hence be used in triplex based modification of genomic DNA.

Inducible DNA alkylation has now been demonstrated by integrating the principles of organic chemistry and antisense technologies. In this manner, inducibly reactive 1,4-dimethyl anthraquinone has been delivered to target sites by a complementary oligodeoxynucleotide and then converted to a highly reactive anthraquinone-methide through irradiation, ultimately producing conjugation with nucleophilic groups of target strands. The cross-linking reactions have been demonstrated to be quite efficient (38% at 10 nM and 45% at 2.2 µM of DNA), highly site specific (first unpaired base), and highly base discriminating (C>T>>A, G). See Example 7, below.

The following Examples further illustrate the various features of the invention, and are not intended in any way to limit the scope of the invention which is defined in the appended claims.

Materials and Method for the Synthetic Procedures

Reactions were carried out under nitrogen atmosphere, with freshly distilled solvents, and were monitored with Machery-Nagel polygram Sil G/UV pre-coated silica gel plates. Proton magnetic resonance ($^1$H NMR) spectra were obtained in deuteriochloroform ($CDCl_3$) with a General Electric QE-300 spectrometer. TMS was used as a reference. Mass spectra were obtained with a Hewlett-Packard HP598A mass spectrometer. Disposable pipets (2 mL) were used as columns in small scale reactions to prevent the loss of materials. Flash silica chromatography is a commonly used purification technique, and is described, for example, by Still et al., *J. Org. Chem.*, 43, 2923–2925 (1978). A gradient of eluent was used for flash silica column chromatography to obtain maximum $\Delta R_f$.

Material and Methods for Coupling Procedures

Oligonucleotides were synthesized by standard solid phase phosphoramidite methods on a Dupont Coder 300 (Department of Pharmacology, SUNY at Stony Brook) and on a Biosearch instrument by Clontech Laboratories, Inc. (Palo Alto, Calif.). When necessary, the oligonucleotides were also purified and deprotected by standard procedures. Reverse phase (C-18) separation and analysis utilized a Varian 5000 HPLC controller, Varian 2050 variable wavelength detector, Hewlett Packard 3390A recording integrator and Spherex 5 µM C-18 column (Phenomenex). UV/VIS spectra were recorded on a Perkin Elmer Lambda-5 spectrophotometer.

EXAMPLE 1

Synthesis of $D-Me_2AQ$. A photochemically activated anthraquinone derivative, 1,4-dimethylanthraquinone ($Me_2AQ$) was prepared in accordance with the invention. The steps of the synthesis are shown in Scheme 1, illustrated in FIG. 1.

Pyridiniumdichromate (PDC). PDC was prepared according to Corey et al., *Tet. Letts.*, 20, 399 (1979) by adding pyridine (20 mL) slowly to a cooled solution of 25 g (0.25 mole) $CrO_3$ in 25 mL of water. The solution was then diluted with 100 mL of acetone and cooled to −20° C. The solidified PDC was collected, washed with cold acetone, and recrystallized in acetone.

Tris(triphenylphosphine)-rhodium(I)chloride. Tris (triphenylphosphine)-rhodium(I)chloride was prepared according to Wilkinson et al., *J. Chem. Soc.(A.)*, 1711 (1966) by adding a solution of rhodium trichloride trihydrate (60 mg, 0.29 mmole) in 3 mL of hot ethanol to a solution of freshly recrystallized ($PPh_3$) (360 mg, 1.37 mole) in 10 mL of hot ethanol. The solution was then refluxed for 30 minutes, filtered, and the burgundy-red crystals of the complex were washed with 10 mL of degassed ether and dried in vacuo to give 188 mg in 91% yield.

4-Pentynoic acid. 4-Pentynoic acid was prepared by adding 4-pentyn-1-ol (100 mg, 1.19 mmole) to a solution of acetic anhydride (343 mg, 3.36 mmole) in 3 mL of pyridine along with a catalytic amount (3 mg) of hexamethylphosphoramide (HMPA) at 0° C. After 10 minutes, the reaction temperature was raised to ambient temperature and the solution was further stirred for 9 hours. Then, the reaction mixture was evaporated and purified with flash column chromatography to give 131 mg of 4-pentynoic acid in 87% yield. $^1$HNMR (300 MH$_2$, $CDCl_3$) δ 4.21(2H,t), 2.28 (2H, m), 2.02–1.84(6H,m).

Coupling of diketo compound with Wilkinson's catalyst (Compound 1.1 in Scheme 1). This compound was prepared by the method of Muller et al., *Tet. Letts.*, 5271 (1970). 1,2-(1-Oxo-2-butynyl)-benzene (40 mg, 0.2 mmole), synthesized according to the method of Muller et al., was added to tris(triphenylphosphine)rhodium(I) chloride (180 mg, 0.2 mmole) in 2 mL of benzene under nitrogen at room temperature. After stirring for 50 hours, the reaction mixture was evaporated and the residue was redissolved in ethyl acetate. Flash silica column chromatography was performed to yield 24 mg of Compound 1.1 as a brown solid (14.6%). $^1$H NMR (300 MHz, CDCl$_3$) δ 8.04–7.37 (34H, m), 2.10 (6H,s).

2-Acetoxypropyl-1,4-dimethyl-anthraquinone (Compound 1.2). The rhodium complex (Compound 1.1) (24 mg, 29 μmole) was added to 5-acetoxypentyne (4 mg, 31 μmole) in 2 mL of benzene. After 15 hours at 50° C., the reaction mixture was evaporated and redissolved in a solution of hexane and ethylacetate (1 to 1 ratio). The product (compound 1.2) was purified by flash silica column chromatography to yield 4 mg (45%). $^1$H NMR (300 MHz, CDCl$_3$) δ 8.11 (2H, m), 7.65 (2H, m), 7.32 (1H, s), 4.19 (2H, t), 2.76 (2H, t), 2.75 (6H, s), 2.11 (3H, s), 1.91 (2H, m).

1,4-Dimethyl-2-hydroxypropyl-anthraquinone (Compound 1.3). The acetoxy compound (Compound 1.2) (4 mg, 14 μmole) was dissolved in 4 mL of a solution of 5% K$_2$CO$_3$ and methanol (1 to 1 ratio). After 6 hours of stirring at room temperature, the reaction mixture was evaporated to half of the original volume for CHCl$_3$-H$_2$O extraction. Then, the organic layer was dried over MgSO$_4$ and filtered, and the solvent was removed under reduced pressure. Purification by flash silica column chromatography yielded the hydroxy compound (Compound 1.3) in quantitative yield. $^1$H NMR (300 MHz, CDCl$_3$) δ 8.04 (2H, m), 7.55 (2H, m), 7.31 (1H, s), 4.45 (1H, t), 3.42(2H, m), 2.95 (2H, t), 2.69 (6H, s), 1.64 (2H, m).

1,4-Dimethylanthraquinonyl-3-propionic acid (Compound 1.4). The hydroxy compound (Compound 1.3) (4 mg, 14 μmole) and PDC (184 mg, 49 μmole) were dissolved and stirred in 2 mL of dimethyl formamide (DMF). After 10 hours at room temperature, 15 mL of H$_2$O was added to the reaction mixture for diethylether extraction. The organic layer was dried over MgSO$_4$ and filtered, and the solvent was removed under reduced pressure. The acid derivative (Compound 1.4) was purified by flash silica column chromatography in a quantitative yield. $^1$H NMR (300 MHz, CDCl$_3$) δ 10.58 (1H, s), 8.14 (2H, m), 7.68 (2H, m), 7.36 (1H, s), 4.69 (2H, t), 4.30 (2H, t), 2.77 (6H, s).

N-Hydroxysuccinimide ester of 1,4-dimethylanthraquinonyl-3-propionic acid (Compound 1.5). The acid derivative (Compound 1.4) (4 mg, 13 μmole), N-hydroxysuccinimide (18 mg, 16 μmole), and 1-ethyl-3-(3-dimethylaminopropyl)carbodiimide (2 mg, 13 μmole) were dissolved in 40 μL of DMF. After 14 hours at 4° C., the reaction mixture was evaporated and the residue was redissolved in 3 mL of H$_2$O for CH$_2$Cl$_2$ extraction. Then, the organic layer was dried over MgSO$_4$ and filtered, and the solvent was removed under reduced pressure. Flash silica column chromatography was performed to yield 4 mg of activated ester (Compound 1.5) (75%). $^1$H NMR (300 MHz, CDCl$_3$) δ 8.13 (2H, m), 7.67 (2H, m), 7.37 (1H, s), 3.17 (2H, t), 2.88 (2H,t), 2.80 (4H, s), 2.72 (6H, s).

A targeted anthraquinone derivative D-Me$_2$AQ was then prepared by coupling the anthraquinone derivative Me$_2$AQ to an oligodeoxynucleotide amino linker moiety (D-C$_6$NH$_2$) as follows:

Preparation of the oligonucleotide (Donor, D) derivatized at the 5' terminus with a hexamethylamino linker group. The hexamethylamino linker was attached to the 5' end of the nascent oligonucleotide (5'-ACGTCAGGTGGCACT (SEQ ID NO:1), hereinafter designated "Donor" or "D"), during the last step of the solid phase synthesis, by using a monomethyoxytrityl protected hexamethylamino precursor (N-MMT-CG-AminoModifier supplied by Clontech Laboratories, Inc.). The protecting group was released after the complete synthesis by treating the crude material with 80% acetic acid for 30 minutes. The free trityl derivative was removed by ether extraction and the oligonucleotide aminolinker derivative (D-C$_6$NH$_2$) was stored as an aqueous solution (−20° C.) before coupling to the reactive centers.

Coupling of oligodeoxynucleotide to the anthraquinone derivative (D-Me$_2$AQ). The 15 base oligodeoxynucleotide carrying a hexamethylamino linker (D-C$_6$NH$_2$) (A$_{260}$=1.2 units, 9 nmole) in 20 μL of 3-(N-morpholino)-propanesulfonic acid (MOPS) (pH 7.5, 0.25M) was added to the activated ester derivative of 1,4-dimethyl-anthraquinone (Me$_2$AQ) (Compound 1.5 of Example 1) (2 mg, 5 μmole) in 20 μL of DMF and kept undisturbed at room temperature for 4 hours. The reaction was analyzed and D-Me$_2$AQ (1,4-dimethylanthraquinone coupled to oligodeoxynucleotide) was purified by reverse phase HPLC (C-18 Spherex column) using a gradient of 45mM triethylamine acetate (pH 6), 10% acetonitrile to 35 mM triethylamine acetate (pH 6), 30% acetonitrile in 30 minutes at a flow rate of 1 mL per minute. D-C$_6$NH$_2$ eluted at 13 minutes while the coupled product eluted at 19 minutes. The product, D-Me$_2$AQ, was isolated in 34% yield as estimated by the recovery of A$_{260}$ units. The D-Me$_2$AQ targeted anthraquinone has the following structure:

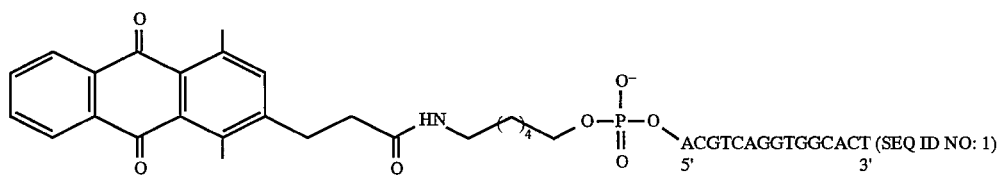

EXAMPLE 2

Target strands of DNA were prepared by solid phase synthesis, as described for the donor oligonucleotide probe prepared in Example 1. These target strands were synthesized to contain a 15 nucleotide segment exactly complementary to the donor oligonucleotide strand (SEQ ID NO:1), but, in addition, having an "overhang" region of three or five nucleotides at the 3' end of the strands for which there is no corresponding sequence in the donor strand. Each of these strands is designated according to the sequence of the overhang region. The target strands are listed in Table 1.

TABLE 1

| NAME | SEQUENCE |
| --- | --- |
| TCTAAG | 5'-AGTGCCACCTGACGTCTAAG (SEQ ID NO:2) |
| TAAG | 5'-AGTGCCACCTGACGTAAG (SEQ ID NO:3) |

TABLE 1-continued

| NAME | SEQUENCE |
| --- | --- |
| TCAG | 5'-AGTGCCACCTGACGTCAG (SEQ ID NO:4) |
| TGAG | 5'-AGTGCCACCTGACGTGAG (SEQ ID NO:5) |
| TTAG | 5'-AGTGCCACCTGACGTTAG (SEQ ID NO:6) |
| DONOR (D) | 3'-TCACGGTGGACTGCA (SEQ ID NO:1) |

5'-End labeling of oligodeoxynucleotides (target strands). The oligodeoxynucleotides ($A_{260}$=0.05 units) were labelled with radioactive phosphorus ($^{32}$p) by treating each strand with $\gamma$—$^{32}$P—ATP (50 μCi, specific activity of 3,000 Ci/mmole) and T-4 polynucleotide kinase in kinase buffer (0.05M tris-HCl pH 7.5, 0.01M $MgCl_2$, 5 mM DTT (dithiothreitol), 0.1 mM EDTA, and 0.1 mM spermidine) for 45 minutes at 37° C. The reaction mixture was diluted to 2 mL with $H_2O$ and centrifuged in a Centricon-10 (10,000 MW cut-off) from the Amicon Division of W. R. Grace & Co., Danvers, Mass., to remove the excess salt and unincorporated $\gamma$—$^{32}$P—ATP. The dilution and centrifugation steps were repeated two more times.

Photolysis of TCTAAG (target strand) (SEQ ID NO:2) and D-Me$_2$AQ (targeted AQ derivative). The targeted anthraquinone derivative linked to an oligodeoxynucleotide (D-Me$_2$AQ) was first annealed to the target strand designated TCTAAG (SEQ ID NO:2) and irradiated under aerobic conditions. 1.1 μM of D-Me$_2$AQ and 0.22 μM of TCTAAG (SEQ ID NO:2) (target strand) containing radiolabelled oligodeoxynucleotides were mixed in 10 mM potassium phosphate buffer (pH 7) (100 μL reaction volume) and left for 5 minutes at room temperature. The annealed duplexes were then irradiated in a pyrex tube at the focal point of 150 watt xenon arc lamp using a 335 nm long pass band filter. The irradiated duplexes were then analyzed by 20% polyacrylamide gel electrophoresis (PAGE) under denaturing conditions (7M urea). Then, the gel was dried and an autoradiogram was taken, illustrated in FIG. 2-A. Lanes 1–7 correspond to 0, ½, 1, 10, 30, 60, and 120 minutes of irradiation, respectively.

Figure 2:
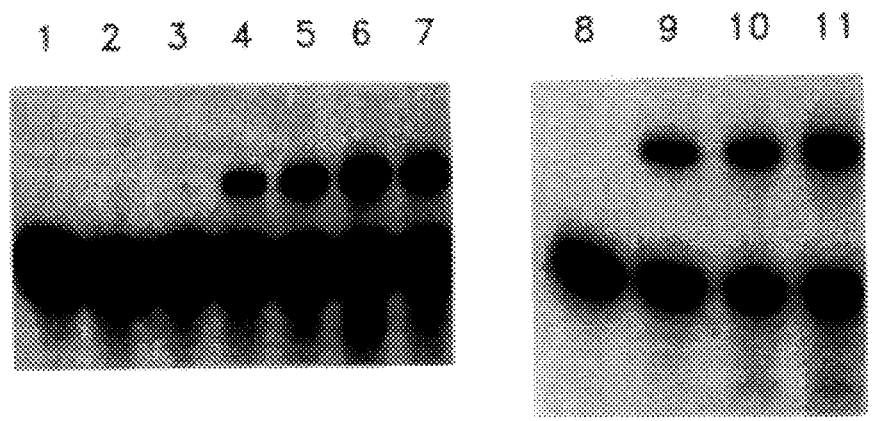
FIG. 2 is an autoradiogram of a denaturing polyacrylamide gel illustrating the formation of a cross-linked DNA product as a function of duration of irradiation of an oligodeoxynucleotide target molecule and a targeted anthraquinone derivative of the invention.

While no oxidative strand scission was detected, a high molecular weight species, estimated to be of a size equivalent to the covalently cross-linked form of two strands, accumulated over the irradiation times of 10, 30, 60, 120 minutes (FIG. 2-A: Lanes 4–7).

The advantage of anthraquinone over naphthoquinone was evident from higher yield (30% yield at 2.2 μM of both strands and 45% at 1.1 μM of D-Me$_2$AQ and 220 nM of TCTAAG) (SEQ ID NO:2) and lower DNA concentration needed for reaction (15% yield at 10 nM of both strands). This is likely the result of a stability difference between the two quinones under the reaction conditions. The naphthoquinone derivative lost all activity after 10 minutes of irradiation, while the anthraquinone derivative lost only 50% of its activity after an hour of irradiation. Details concerning the behavior of naphthoquinones may be found in U.S. application Ser. No. 07/442,947 (see also FIG. 3, as described below).

Addition of excess D-Me$_2$AQ enhanced alkylation of TCTAAG (SEQ ID NO:2) to the extent that irradiating a mixture of 100nM D-Me$_2$AQ and 10 nM TCTAAG (SEQ ID NO:2) produced 38% alkylation after 2 hours (FIG. 2-B). In FIG. 2-B, lanes 8–11 correspond to 0, 30, 60 and 120 minutes of irradiation respectively. These results can be explained as a facilitation of the reaction caused by the excess D-Me$_2$AQ exchanging with any inactivated form of D-Me$_2$AQ accumulated during the irradiation. In addition, a high overall concentration of DNA would be expected to enhance the conversion by maximizing the hybridization of the complementary sequence.

Figure 3:
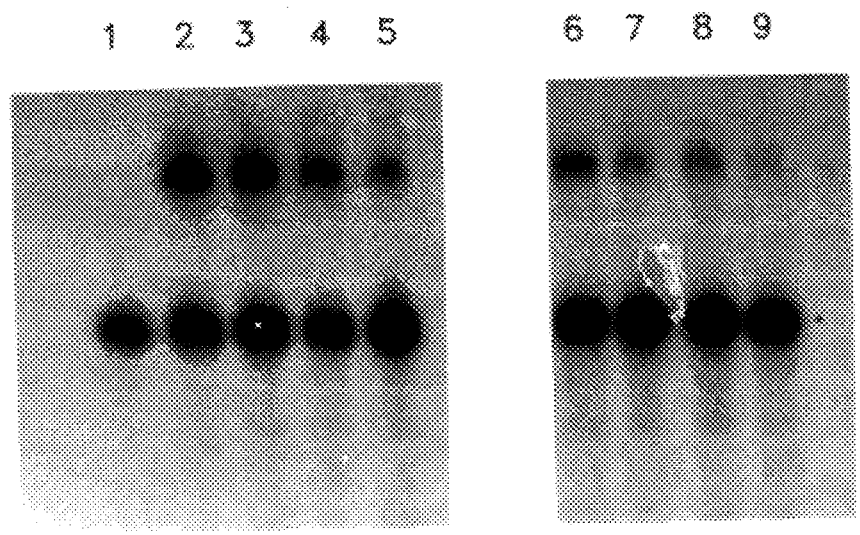
FIG. 3 is an autoradiogram of a denaturing polyacrylamide gel illustrating the effect of preirradiation of a targeted anthraquinone derivative of the invention on the ability of the anthraquinone to cross-link oligodeoxynucleotide target molecule.

Preirradiation of D-Me$_2$AQ, prior to hybridization with TCTAAG (SEQ ID NO:2), slightly inhibited the formation of the product upon later irradiation of the full duplex. The suppression of activity was more severe when preirradiation was performed in $D_2O$ rather than $H_2O$ (FIG. 3). These results suggest that the anthraquinone is slowly inactivated over the course of hours of irradiation and that diffusible singlet oxygen ($^1O_2$) is in part responsible for the deactivation of the anthraquinone moiety.

In FIG. 3, Lane 1 is a control lane: no irradiation; Lanes 2–5 correspond to preirradiation durations of 0, 30, 60, and 120 minutes in $H_2O$, respectively; Lanes 6–9 correspond to preirradiation durations of 0, 30, 60, and 120 minutes in $D_2O$, respectively.

EXAMPLE 3

The effect of irradiation wavelength on the efficacy of DNA target strand modification by the targeted AQ derivative, D-Me$_2$AQ, was evaluated. D-Me$_2$AQ was annealed to target DNA, i.e., TCTAAG. The annealing was accomplished using a 100 μL reaction volume containing 2.2 μM D-Me$_2$AQ and 2.2 μM TCTAAG (SEQ ID NO:2) in 10 mM phosphate buffer (pH 7). The reagents were mixed and left to stand for 5 minutes at room temperature (22° C.). These samples were exposed to radiation for periods ranging up to 2 hours. Radiation wavelength was controlled using long pass filters with cut-offs at 335 nm, 320 nm, and 305 nm to selectively activate the AQ moiety ($\lambda_{max}$=340 nm) while defining the effect of radiation induced strand scission of DNA ($\lambda_{max}$=260 nm). The reactions were analyzed by polyacrylamide gel electrophoresis. Autoradiograms were taken and are shown in FIG. 4.

Figure 4:
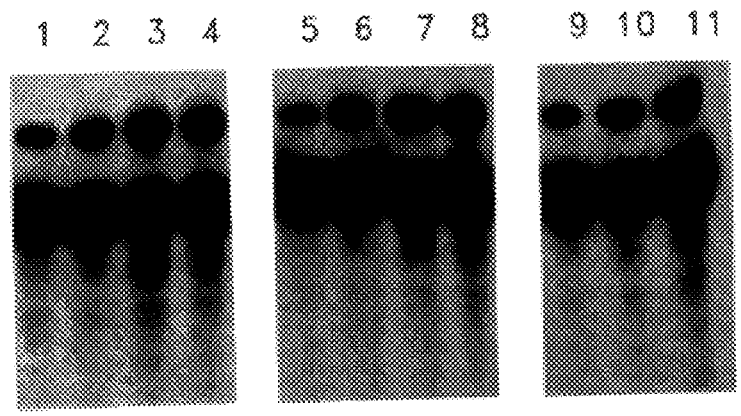
FIG. 4 is an autoradiogram of a denaturing polyacrylamide gel illustrating the effect of radiation wavelengths on the cross-linking efficiency of a targeted anthraquinone derivative of the invention.

In FIG. 4, each lane of the gel corresponds to different conditions as follows:

Lane 1: 335 nm filter; 10 minutes photolysis;
Lane 2: 335 nm filter; 30 minutes photolysis;
Lane 3: 335 nm filter; 1 hour photolysis;
Lane 4: 335 nm filter; 2 hours photolysis;
Lane 5: 320 nm filter; 10 minutes photolysis;
Lane 6: 320 nm filter; 30 minutes photolysis;
Lane 7: 320 nm filter; 1 hour photolysis;
Lane 8: 320 nm filter; 2 hours photolysis;
Lane 9: 305 nm filter; 10 minutes photolysis;
Lane 10: 305 nm filter; 30 minutes photolysis;
Lane 11: 305 nm filter; 1 hour photolysis If oxidation of the DNA target strand were to have occurred, strand scission should have been detectable as the formation of small fragments on the autoradiograms. No such scission was observed. Instead, a larger fragment was observed in each case, attributable to cross-linking of the DNA through the photoenolization of the Me$_2$AQ moiety. The yield of cross-linking was improved by using a 320 nm filter over a 335 nm filter, but the use of a 305 nm filter produced noticeable random degradation after one hour of photolysis (lane 11). Accordingly, light of wavelengths between 320 nm and 420 nm is preferred for activation of the alkylating agents of the invention which are photochemically activated.

EXAMPLE 4

To establish whether the observed cross-linking by D-Me$_2$AQ results from conditions other than photolysis, samples of duplexes (100 nM of D-Me$_2$AQ and 10 nM of two target strands: TCAG (SEQ ID NO:4); TTAG (SEQ ID NO:6)) in 10 µL of various reaction solutions. Then, the reaction mixtures were dialyzed and lyophylized for analysis by PAGE. Only photolysis produced the cross-linked product. The results of this study are illustrated in FIG. 5.

Figure 5:
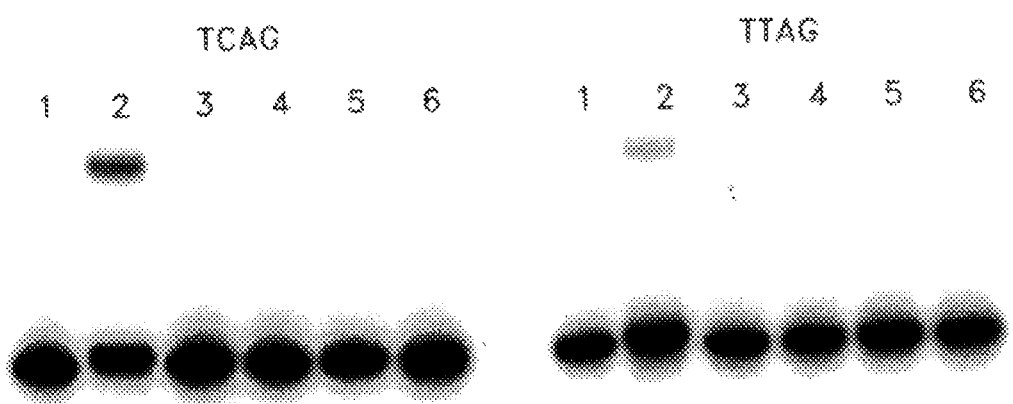
FIG. 5 is an autoradiogram of a denaturing polyacrylamide gel illustrating the base specificity of the cross-linking of oligodeoxynucleotide target strands by a targeted anthraquinone derivative of the invention.

In FIG. 5, each lane in the gel corresponds to different reaction conditions as follows:

Lane 1: Control: No treatment; 10 mM potassium phosphate buffer (pH 7);

Lane 2: Photolysis: Irradiation (λ>335 nm) for 60 minutes in 10mM potassium phosphate buffer (pH 7);

Lane 3: Acid: 0.25M Piperidine formate (pH 2) for 60 minutes at room temperature;

Lane 4: Base: M Triethylammonium acetate (pH 11) for 60 minutes at 37° C.;

Lane 5: Heat: 90° C. for 60 minutes in 10 mM potassium phosphate (pH 7);

Lane 6: 100 mM NaBH$_4$ in 10 mM potassium phosphate (pH 7) for 60 minutes at room temperature, then quenched with 5 µL of 50 % acetic acid.

EXAMPLE 5

The cross-linked products of Example 5 were subjected to further irradiation and chemical analyses relating to the effects of acid, acid/piperidine, piperidine, heat, and basic conditions on the stability of the cross-linking.

Purification of cross-linked product. After photolysis/PAGE, an autoradiogram was taken directly from the wet gel, illustrated in FIG. 5. The gel parts containing each cross-linked product, i.e., Lane 2 from each gel shown in FIG. 5, were sliced off, crushed and treated with 300 µL of elution buffer (5 mM Tris, 2.5 mM acetic acid, and 0.25M NaCl) for 4 hours at 4° C. The mixtures were then centrifuged for 10 minutes and the supernatants were recovered. To the recovered supernatants, 150 µL of ammonium acetate (7.5 M) and 1 mL of ethanol were added. After 12 hours at -20° C., the mixtures were centrifuged for 10 minutes at 4° C. The DNA precipitates were washed with 75% ethanol. The remaining DNA was redissolved in 1.5 mL of H$_2$O and centrifuged in an Amicon concentrator (10,000 MW cut off) to remove any remaining salts.

Sequencing standard for G nucleotides in the target strands.

1 µL of dimethylsulfate was added to 50 nCi of DNA in 60 mL of H$_2$O, followed immediately by the addition of 20 µL of β-mercaptoethanol. The mixture was then dialyzed for 3 hours and lyophilized. 60 µL of H$_2$O and 1 µL of piperidine were then added to the remaining solid, and the reaction was allowed to proceed for 30 minutes at 90° C. The mixture was then lyophilized.

Figure 6:
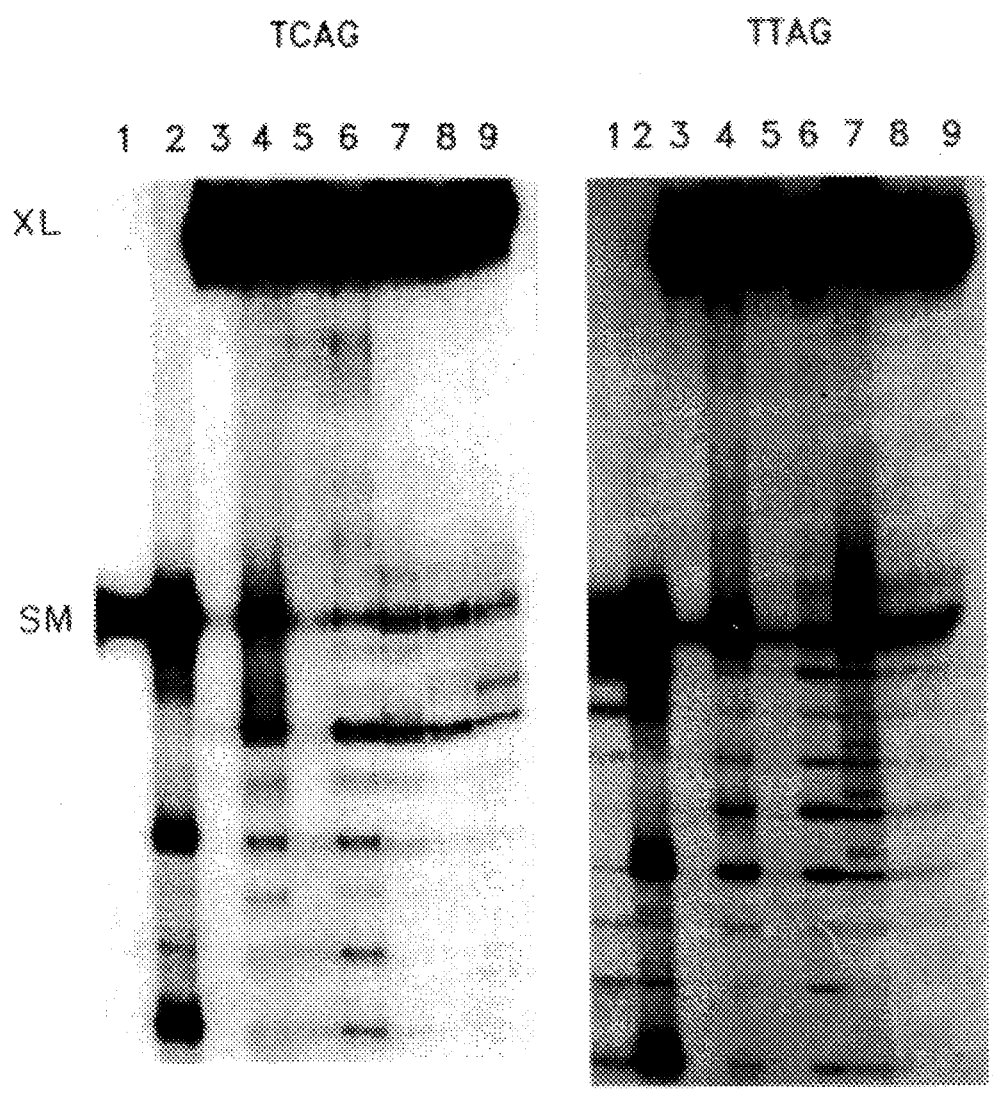
FIG. 6 is an autoradiogram of a denaturing polyacrylamide gel illustrating the stability of oligodeoxynucleotide target molecules cross-linked by a targeted anthraquinone derivative in various chemical conditions.

Product characterization. As shown in FIG. 6, purified cross-linked products were subjected to various conditions. Then samples were analyzed by PAGE, illustrated in FIG. 6. In FIG. 6, the lanes in each gel correspond to the following reaction conditions:

Lane 1: Control: Target strand only;

Lane 2: Sequencing standard for G nucleotides of target strand;

Lane 3: Control: Untreated cross-linked product;

Lane 4: Irradiation (λ>335 nm) for 60 minutes in 10 mM potassium phosphate (pH 7);

Lane 5: 0.25 M piperidine formate (pH 2) for 60 minutes at 37° C.;

Lane 6: same as lane 5, then lyophilized;

Lane 7: i M piperidine for 30 minutes at 90° C.;

Lane 8: 90° C. for 30 minutes in 10 mM potassium phosphate (pH 7);

Lane 9: 0.1M triethylammonium acetate (pH 11) for 60 minutes at 37° C.

The cross-linked products of irradiation were then separated from the reaction mixtures by preparative gel electrophoresis, according to the method described in McDonnell et al., *J. Mol. Biol.*, 110, 119 (1977), and subjected to further irradiation and chemical analysis. The newly formed bond between the DNA strands proved to be quite stable under acidic conditions (0.25M piperidine formate, pH 2, 1 hour at 37° C.). However, the reverse reaction of the cross-linked duplex back to starting target strands and to species migrating in a manner similar to a 16 base oligodeoxynucleotide (reaction occurs at the 16th base of the target) was seen in cases of further irradiation and treatment with base (0.1M triethylammonium acetate, pH 11, 30 minutes at 90° C.). The cross-linked product produced in the alkylation of thymidine (TTAG (SEQ ID NO:6)) was more stable than that from alkylation of cytidine (TCTAAG (SEQ ID NO:2) and TCAG (SEQ ID NO:4)) under either treatment.

EXAMPLE 6

Figure 7:
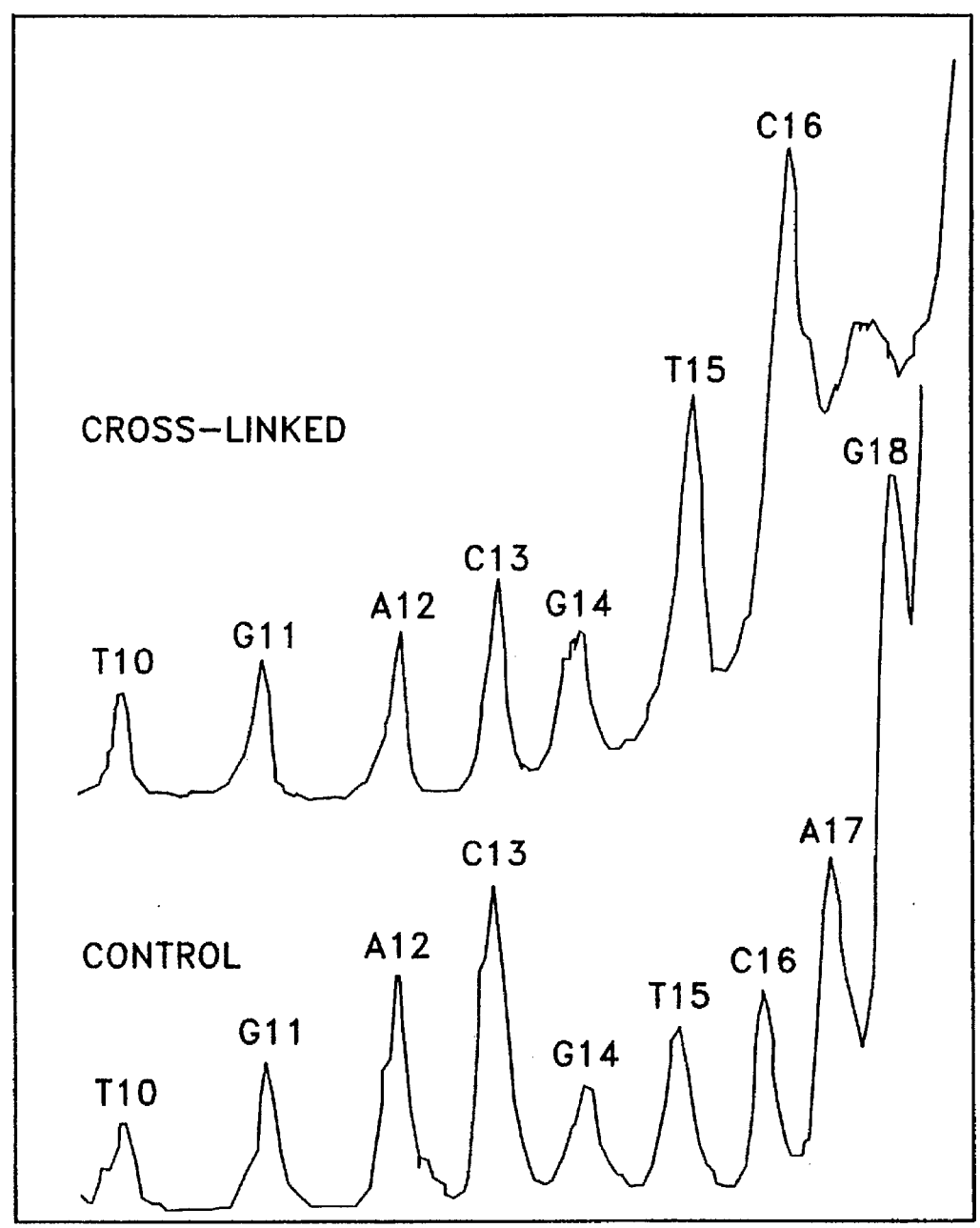
FIG. 7 is a densitometric plot of an autoradiogram of a denatured polyacrylamide gel illustrating that the cross-linking of an oligodeoxynucleotide target molecule by a targeted anthraquinone derivative of the invention occurs at the first unpaired base of the target strand.

Hydroxyl radical footprinting indicates that TCAG is alkylated at the first unpaired base. 5 nCi of purified cross-linked product was treated with 10 mM Tris (pH 7.5), 5 mM Fe(II), 20 mM EDTA, and 20 mM L-ascorbic acid in 60 µL of final volume. After 5 minutes at room temperature, 1 µL of H$_2$O$_2$ (3 mM) was added and the mixture was incubated for 3 minutes at room temperature. 5 µL of thiourea (1M) was then added to the mixture for incubation of 10 minutes. The reaction mixture was lyophilized for gel analysis. After high resolution polyacrylamide gel electrophoresis (20%) under denaturing conditions (7M urea), an autoradiogram was prepared and then scanned with a densitometer using Gel Scan XL (2.1) program, supplied by LKB-Pharmacia, Piscataway, N.J. The densitometric plot of the autoradiogram is illustrated in FIG. 7.

This footprinting indicated that the alkylation of target strand proceeds at the first unpaired base (C-16 in a target strand of TCAG (SEQ ID NO:4)).

EXAMPLE 7

The reactivity and selectivity of our model reagent D-Me$_2$AQ suggests that target alkylation proceeds through the rapid formation and depletion of an electrophilic intermediate such as an anthraquinone-methide.

Figure 8:
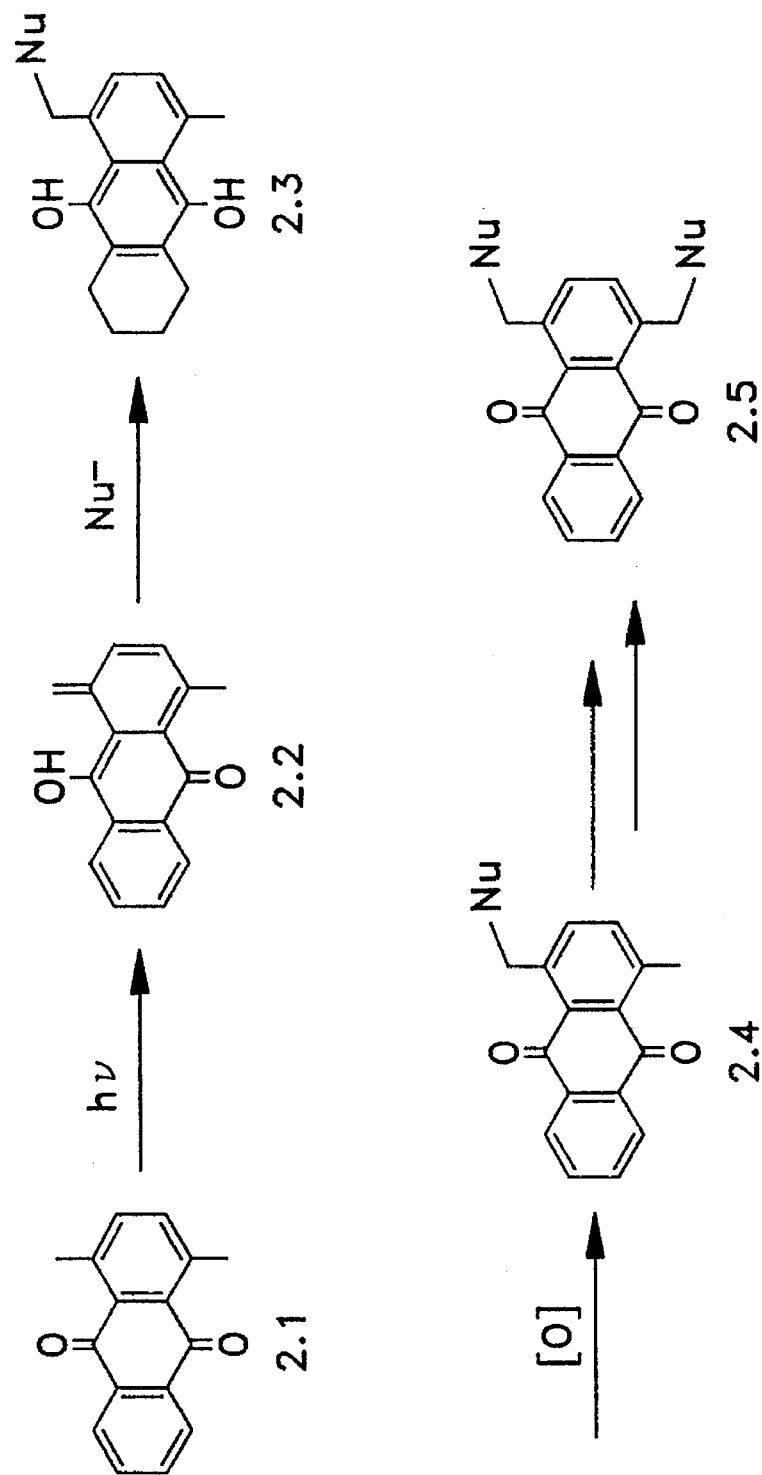
FIG. 8 illustrates a postulated reaction pathway of an anthraquinone derivative of the invention. (Scheme 2).

Scheme 2, shown in FIG. 8, illustrates a postulated reaction pathway. The dimethyl anthraquinone (Compound 2.1) upon irradiation, hv, forms the activated quinone methide (Compound 2.2). The quinone methide is electrophilic. Nucleophilic compounds such as the bases in DNA are natural reaction targets of the quinone methide. A nucleophile, Nu$^-$, reacts with the methide group, forming a covalent linkage (Compound 2.3). Under appropriate conditions the AQ moiety can further alkylate additional nucleophile by the formation of a second quinone methide. This reaction is carried out when O$_2$ in the environment spontaneously oxidizes (shown by [O] in Scheme 2) Compound 2.3 to yield Compound 2.4. Then, in a reaction sequence similar to the conversion of Compound 2.1 to Compound 2.3, irradiation of Compound 2.4 produces a reactive quinone methide, which further reacts with another nucleophile, for instance another base in a second DNA strand. In the case of duplex or triplex DNA, the AQ can effectively cross-link two or more strands, as exemplified by the reoxidized Compound 2.5. This sequence of oxidation, photochemical activation, and nucleophilic reaction can be repeated in AQ derivatives possessing more than 2 inducible reactive groups according to the invention.

No reaction was detected either in the absence of the anthraquinone moiety on the donor strand or without irradiation.

To determine the nucleophilic base responsible for cross-linking, target strands including a complementary sequence to the donor strand and different bases of A, C, G and T at the first unpaired position of a noncomplementary overhang region have been subjected to the reaction. These target strands are shown in Table 1.

Figure 9:
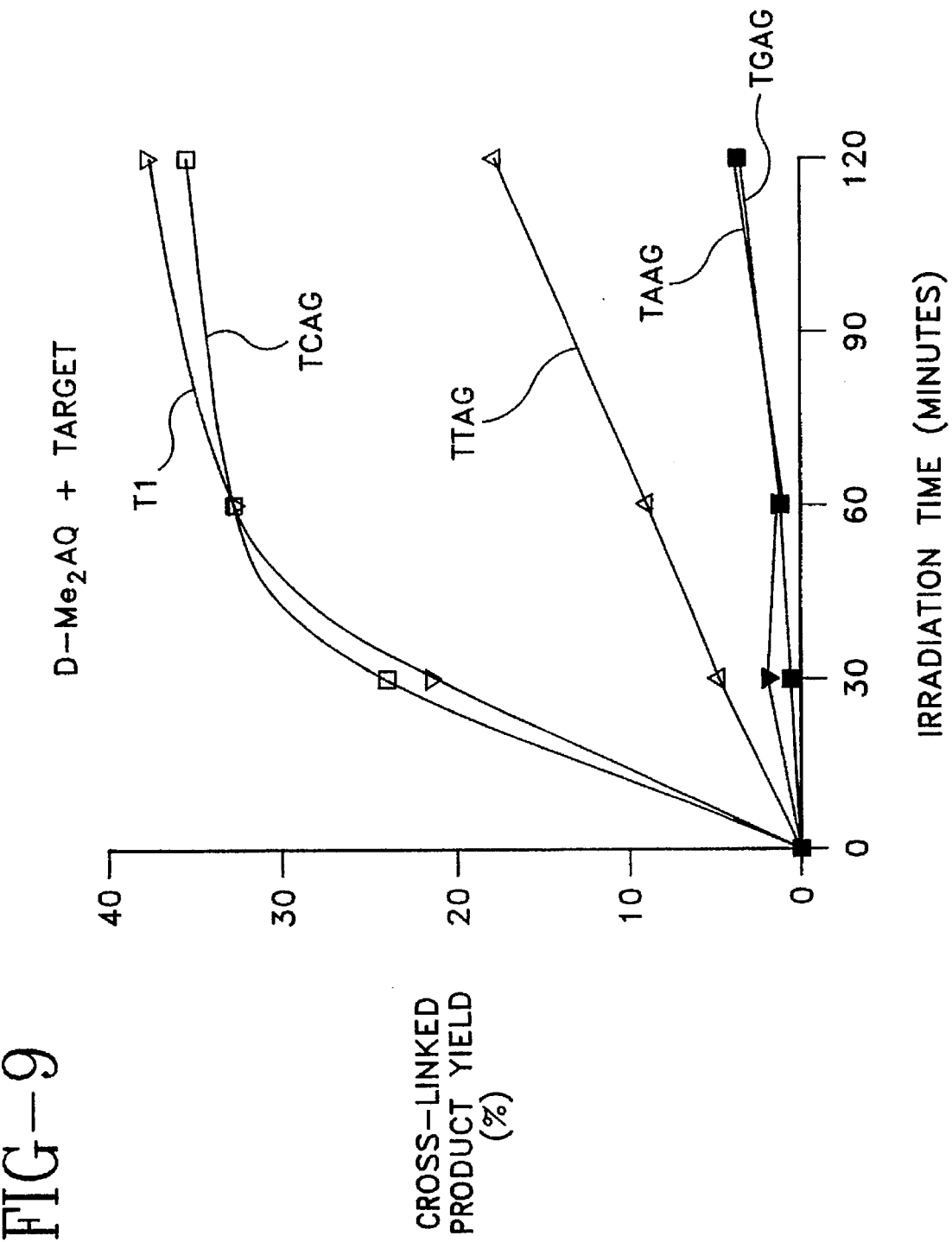
FIG. 9 is a graph illustrating the dependence of the cross-linking reaction of a targeted anthraquinone derivative of the invention with an oligodeoxynucleotide target molecule on length of irradiation, and the base selectivity of the cross-linking reaction.

Reaction mixtures containing D-Me$_2$AQ (50 nM) and each containing one of the five target strands (10 nM) were irradiated for 2 hours at λ>335 nm. Samples were taken at 30, 60, 90, and 120 minutes. The results are shown in FIG. 9. Only the irradiation of D-Me$_2$AP:TCAG (SEQ ID NO:4) and Donor:TTAG mixtures yielded significant conversion to cross-linked materials. The photolysis of D-Me$_2$AP:TAAG (SEQ ID NO:3) and Donor:D-Me$_2$AQ:TGAG (SEQ ID NO:5) resulted in negligible amounts of cross-linked products. These results imply that only the first unpaired base participates in the cross-linking reaction, that the reactivity of the bases differs, in the order of C>T>>A and G. This expected base alkylation was verified by Hopkins's method of footprinting, and the sites of attachment may be C-20, T-4O, T-3N, and C-4NH$_2$ See Singer et al., *Molecular Biology of Mutagens and Carcinogens*, Plenum Press, New York (1983); Blackburn et al., *Nucleic Acids in Chemistry and Biology*, Chapter 7, IRL Press (1990).

Inducible DNA alkylation has been demonstrated by the present invention by integrating the principles of organic chemistry and antisense technologies. In this manner, unreactive 1,4-dimethyl anthraquinone has been delivered to the target sites by a complementary oligodeoxynucleotide and converted to the highly reactive anthraquinone-methide under irradiation for the ultimate conjugation with nucleophilic groups of target strands. The cross-linking reactions have been demonstrated to be quite efficient (38% at 10 nM and 45% at 2.2 µM of DNA), highly site specific (first unpaired base), and highly base discriminating (C>T>>A and G).

EXAMPLE 8

Base specificity of the Me2AQ alkylation was further examined by preparation of a simplified reaction between the untargeted AQ derivative, Me$_2$AQ, and a nucleotide, thymine. 1,4-Dimethylanthraquinone was prepared according to the method described by Rosenfeld et al., "Synthesis of an Isolable Quinodimethane", *J. Chem. Educ.*, 68, 691–692 (1991). N-1 of thymine was alkylated to improve its solubility in acetonitrile.

1,4-Dimethylanthraquinone. 2-(2,5-Dimethylbenzoyl) benzoic acid (2 g, 8 mmole) was added to the 10 mL of cold H$_2$SO$_4$. Once the solid was dissolved, the reaction temperature was raised to 70° C. and the mixture was stirred for 1 hour. The dark red reaction mixture was cooled to room temperature and chilled in an ice bath. The mixture was poured into 50 mL of ice water. The green precipitate was filtered and washed with water, then with 5% Na$_2$CO$_3$ (until foaming stopped), and again with water. The product was purified by flash silica column chromatography to yield a bright yellow solid in 75% yield. The compound was recrystallized twice from a 2:1 mixture of hexane and ethyl acetate to give bright yellow crystals. $^1$HNMR (300 MHz, CDCl$_3$) δ 8.08 (2H, d), 7.65 (2H, t), 7.31 (2H, s), 2.70 (6H, s). 1-Ethylthymine. NaH (60 %, 320 mg, 8 mmole) was added to thymine (1 g, 8 mmole) in 10 mL of DMF at 80° C. After a white suspension formed, iodoethane (1.24 g, 8 mmole) was added to the mixture. The resulting mixture was stirred at 80° C. for 3 hours. After cooling down the reaction, 30 mL of ethyl acetate was added and the mixture was washed with H$_2$O. The organic layer was dried over MgSO$_4$ and filtered, and the solvent was removed under reduced pressure. Flash silica column chromatography was performed to yield 42% 1-ethylthymine, 36% 3-ethylthymine, and 8% 1,3-diethylthymine. 1-Ethylthymine was recrystallized from a 1:1 mixture of chloroform and hexane to give a white crystalline product. $^1$HNMR (300 MHz, CDCl$_3$) δ 9.36 (1H, broad), 6.99 (1H, s), 3.75 (2H, q), 1.91 (3H, s), 1.29 (3H, t)

Photolysis. 1,4-Dimethylanthraquinone (9 mg, 39 µmole) and 1-ethylthymine (30 mg, 195 µmole) were dissolved in 3 mL of acetonitrile. The mixture was irradiated in a pyrex tube at the focal point of 150 watt xenon arc lamp using a 335 nm long pass band filter. After 40 minutes of irradiation, purification of the reaction mixture yielded one major compound. The product isolated from this reaction was not an AQ-thymine conjugate, but was identified as 1-methyl-4-hydroxymethyl-anthraquinone by nmr and mass spectroscopy. MS (EI) m/z (rel. intensity) 252 (19), 235 (8.17), 221 (25.08), 207 (6), 194 (17.82), 178 (13.14), 165 (100); $^1$H NMR (300 MHz, CDCl$_3$) δ 8.19 (2H, m), 7.97 (1H, d), 7.77 (2H, m), 7.62 (1H, d), 5.67 (2H, s), 2.86 (3H, S).

EXAMPLE 9

Figure 10:
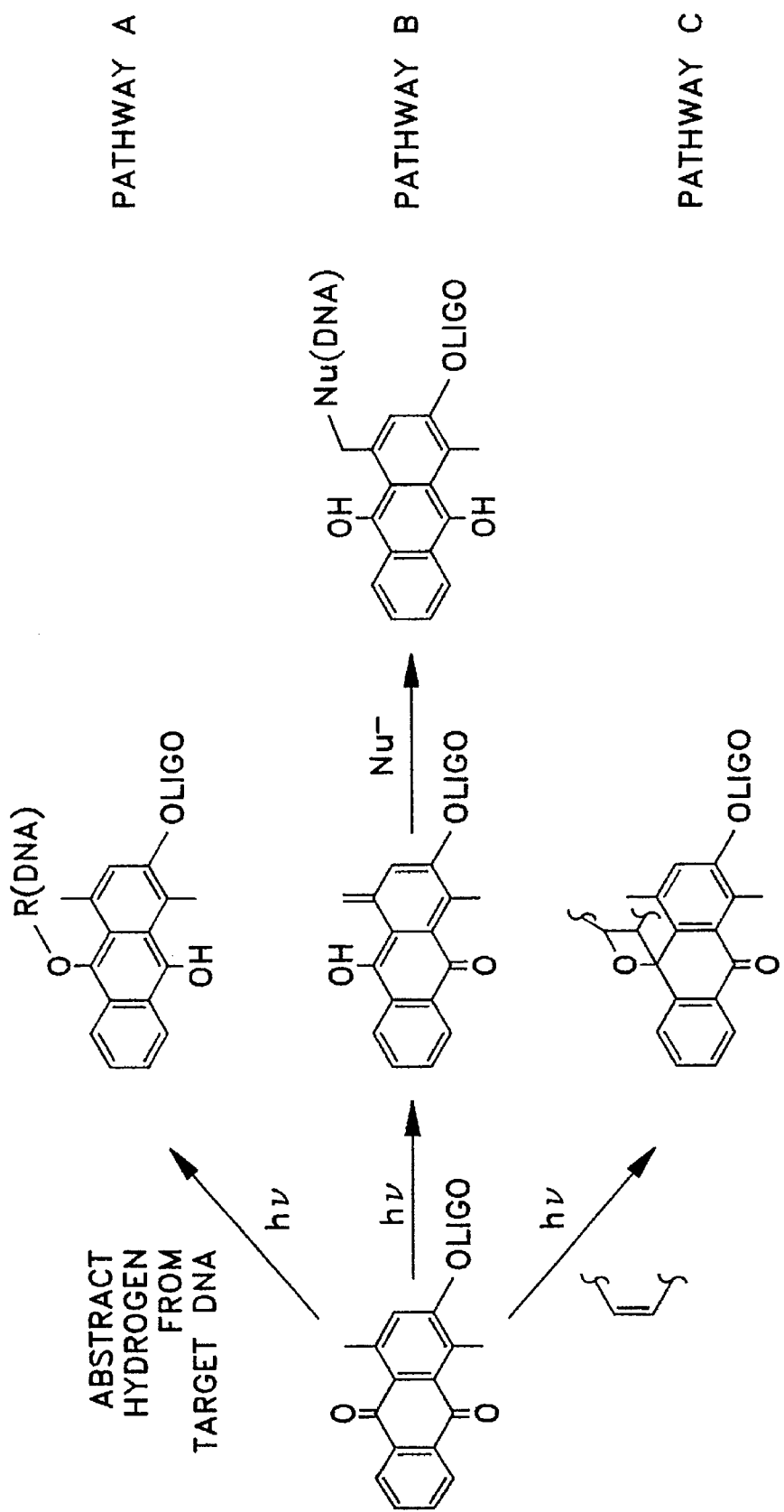
FIG. 10 illustrates potential reaction mechanisms involved in the cross-linking of a target molecule by an anthraquinone derivative of the invention. (Scheme 3).

While the alkylation reaction apparently proceeded through the formation of a quinone methide intermediate, at least two other reaction mechanisms were possible. One alternative, shown as Pathway A in Scheme 3, illustrated in FIG. 10, involves the abstraction of hydrogen from the target nucleic acid, followed by interstrand conjugation. In this hypothetical pathway, the methyl substituents on the AQ ring system would be unnecessary. Indeed anthraquinone has been reported to abstract hydrogen from an alkyl substituent to form an intramolecular conjugation of the alkyl group with the oxygen of a ketone. See Tanimoto et al., "Spectroscopic Studies on the Intramolecular Hydrogen Abstraction Reactions of n-Alkyl Anthraquinone-2-carboxylates", *Bull. Chem. Soc. Jpn.*, 21, 3121–3127 (1988).

Another alternative hypothetical alkylation pathway, shown as Pathway C in Scheme 3, involves a cycloaddition reaction, wherein the carbonyl group of the AQ reacts with the double bonds present in cytidine and thymidine. Again, in this pathway, the methyl substituents present on Me$_2$AQ would be unnecessary.

It was seen that Pathways A and C would be possible even if the methyl groups on Me$_2$AQ were removed, while the methyl groups would be necessary for reaction Pathway B, as originally hypothesized. To distinguish among the pathways, then, it was proposed to synthesize a targeted anthraquinone (D-AQ) similar to the targeted anthraquinone derivative of the invention (D-Me$_2$AQ) but lacking the two methyl groups at positions 1 and 4 of the AQ ring system. If the D-AQ complex failed to alkylate nucleic acid target strands, then Pathways A and C would be ruled out.

Figure 11:
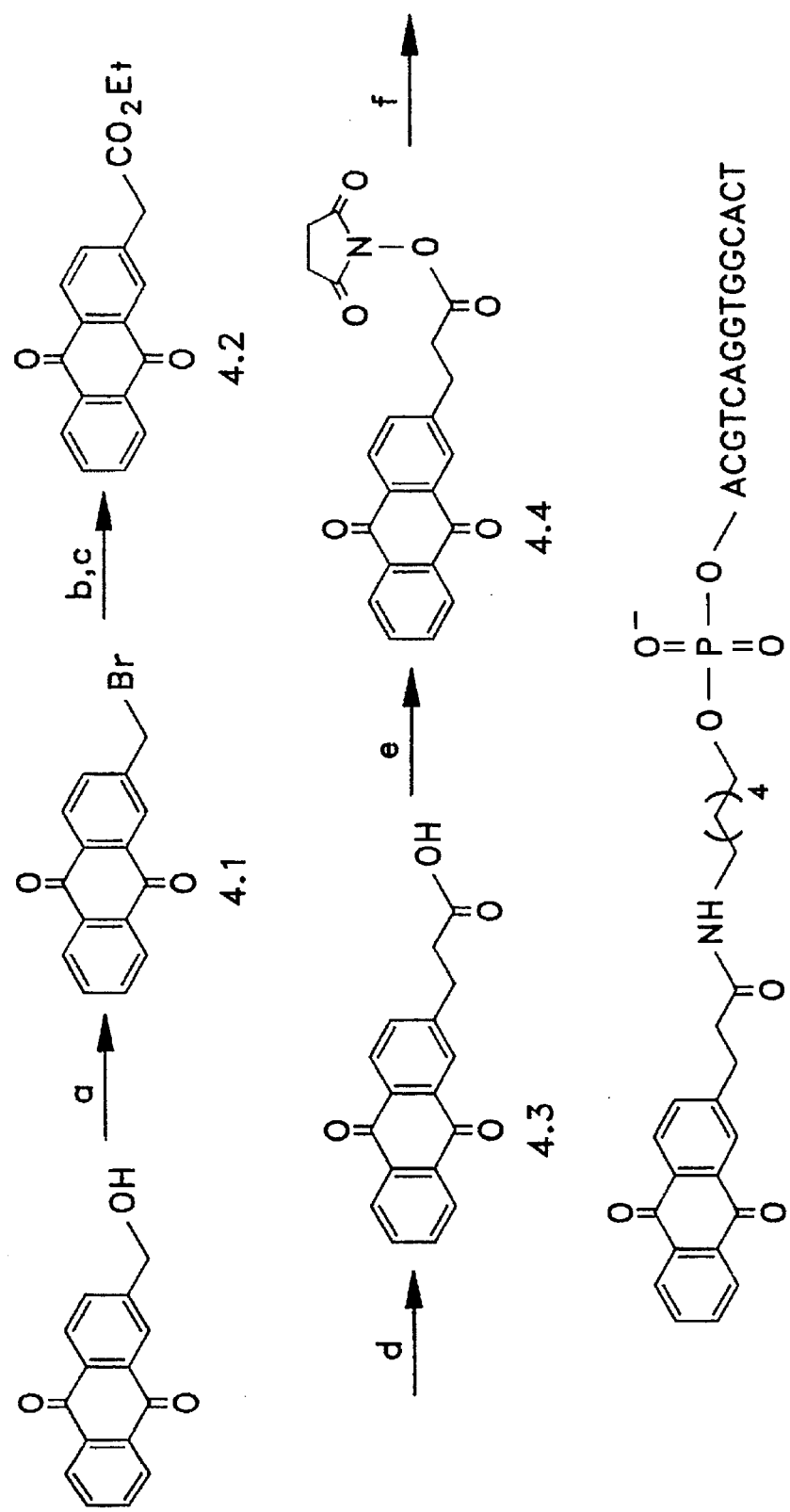
FIG. 11 illustrates a reaction sequence for the synthesis of a targeted anthraquinone molecule. (Scheme 4).

The synthesis of the oligonucleotide-linked anthraquinone (D-AQ) is shown below in Scheme 4, illustrated in FIG. 11.

2-Bromomethylanthraquinone (Compound 4.1). A solution of PBr$_3$ (82 mg, 302 µmole) in 5 mL of tetrahydrofuran (THF) was placed in ice bath. 2-Hydroxymethylanthraquinone (100 mg, 421 µmole) obtained from Aldrich Chemical Co., St. Louis, Miss., in 10 mL of THF was added to the mixture slowly over 10 minutes. After 1 hour at 0° C., the reaction temperature was raised to room temperature and the mixture was stirred for 48 hours. The mixture was evaporated and then redissolved in ethyl acetate for H$_2$O extraction. The organic layer was dried over MgSO$_4$ and filtered, and the solvent was removed under reduced pressure. 2-Bromomethylanthraquinone was purified by flash silica column chromatography (Yield= 52%). $^1$H NMR (300 MHz, CDCl$_3$) δ 8.24 (2H, m), 8.14 (1H, s), 8.01(1H,d), 7.70 (1H, d), 7.57 (2H, m), 4.68 (2H, s).

Diethyl 2-methylanthraquinonylmalonate. Na metal (425 mg, 21.3 mmole) was dissolved in 50 mL of ethanol. To 5 mL of this solution, diethyl malonate (32 mg, 199 µmole) in 5 mL of THF was added, and the mixture was refluxed for 1 hour. 2-bromomethylanthraquinone (Compound 4.1) (50 mg, 166 µmole) in 5 mL of THF was then added to the refluxing reaction mixture. The reaction was refluxed for 8 hours, cooled to room temperature, and then quenched with 5 mL of saturated NH$_4$Cl solution. The mixture was concentrated under vacuum, and redissolved in 20 mL of ethyl acetate for H$_2$O extraction. The organic layer was dried over MgSO$_4$ and filtered, and the solvent was removed under reduced pressure. The residue was purified by flash silica column chromatography to yield 41 mg (54 %). $^1$H NMR (300 MHz, CDCl$_3$) δ 8.11 (2H, m), 7.96 (1H, s), 7.88 (1H, d), 7.64 (1H, d), 7.37 (2H, m), 4.61 (2H, d), 4.20 (5H, m), 1.21 (6H, t).

Ethyl anthraquinonyl-3-propionoate (Compound 4.2). The diethyl ester derivative of anthraquinone (40 mg, 89 µmole) in 1 mL of DMSO (dimethyl sulfoxide) was added to NaCl (21 mg, 356 µmole) in 500 µL of H$_2$O. The mixture was stirred for 28 hours at 140° C. After cooling the mixture, 10 mL of CHCl$_3$ was added for H$_2$O extraction. The organic layer was dried over MgSO$_4$ and filtered, and the solvent was removed under reduced pressure. The crude compound was purified by flash silica column chromatography to yield 20 mg (60 %). $^1$H NMR (300 MHz, CDCl$_3$) δ 8.13 (2H, m), 8.01 (1H, s), 7.90(1H, d), 7.69 (1H, d), 7.44 (2H, m), 4.48 (2H, t), 4.15 (2H, q), 3.77 (2H, t), 1.22 (3H, t).

Anthraquinonyl-3-propionic acid (Compound 4.3). The ethyl ester derivative of anthraquinone (Compound 4.2) (20mg, 53 µmole) was heated in a mixture of 2 mL of aqueous KOH (45 %) and 5 mL of methanol for 6 hours at 80° C. The methanol was evaporated, and the aqueous layer was acidified with HCl (10 %). Then, 10 mL of ethyl acetate was added to the mixture for H$_2$O extraction. The organic layer was dried over MgSO$_4$ and filtered, and the solvent was removed under reduced pressure. The acid compound was purified by flash silica column chromatography to yield 15 mg (81%). $^1$H NMR (300 MHz, CDCl$_3$) δ 11.12 (1H, s), 8.24 (2H, m), 8.n (1H, s), 7.99(1H, d), 7.75(1H, d), 7.56(2H, m), 4.70 (2H, t), 4.33 (2H, t).

N-Hydroxysuccinimide ester of anthraquinonyl-3-propionic acid (Compound 4.4). Anthraquinonyl-3-propionic acid (Compound 4.3) (5 mg, 13 µmole), N-hydroxysuccinimide (18 mg, 16 µmole), and 1-ethyl-3-[3-dimethylaminopropyl]carbodiimide (2 mg, 13 µmole) were dissolved in 40 µL of DMF. After 16 hours at 4° C., the reaction mixture was evaporated and redissolved in 3 mL of H$_2$O for CH$_2$Cl$_2$ extraction. Then, the organic layer was dried over MgSO$_4$ and filtered, and the solvent was removed under reduced pressure. The activated ester was purified by flash silica column chromatography to yield 4 mg (68 %). $^1$H NMR (300 MHz, CDCl$_3$) δ 8.15 (2H, m), 8.01(1H, s), 7.88 (1H, d), 7.67 (1H, d), 7.50 (2H, m), 3.32 (2H, t), 2.88 (2H,t), 2.76 (4H, s).

Coupling of oligodeoxynucleotide with anthraquinone derivative, D-AQ. The 15 base oligodeoxynucleotide amino linker, D-C$_6$NH$_2$ (A$_{260}$=5 units, 38 nmole) in 20 µL of 3-(N-morpholino)propanesulfonic acid (pH 7.5, 0.25 M) was added to the activated ester of anthraquinone derivative (Compound 4.4) (4 mg, 9 µmole) in 20 µL of DMF and kept undisturbed at room temperature for 4 hours. The reaction was analyzed and D-AQ (anthraquinone coupled to oligodeoxynucleotide) was purified by reverse phase HPLC (C-18 Spherex column) using a gradient of 45 mM triethylamine acetate (pH 6), 10% acetonitrile to 35 mM triethylamine acetate (pH 6), 30% acetonitrile in 30 minutes at a flow rate of 1 mL per minute. D-C$_6$NH$_2$ eluted at 13 minutes while the coupled product eluted at 20 minutes. The product, D-AQ, was isolated in 10% yield, as estimated by the recovery of A$_{260}$ units.

EXAMPLE 10

Figure 12:
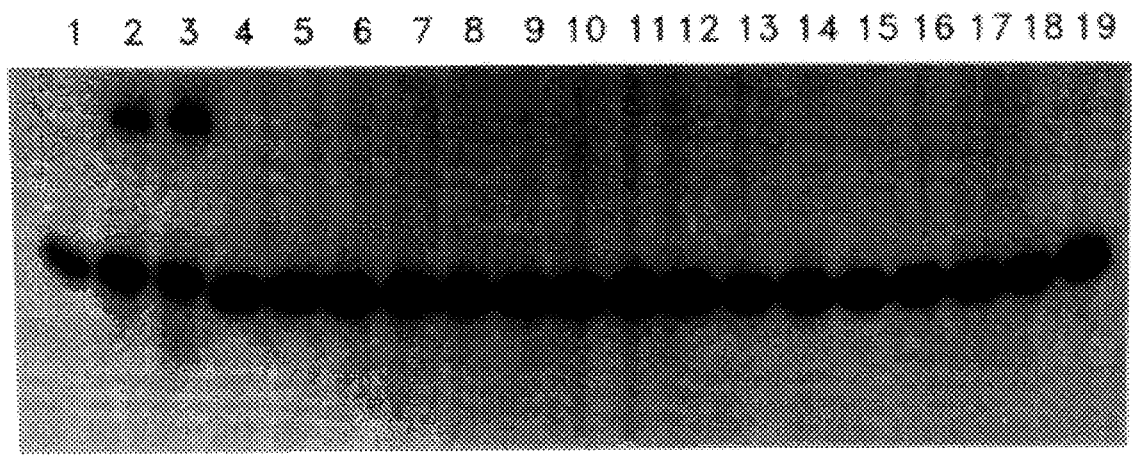
FIG. 12 is an autoradiogram of a denaturing polyacrylamide gel illustrating the inability of a targeted anthraquinone molecule to cross-link an oligodeoxynucleotide target molecule under conditions identical to or similar to conditions sufficient to induce cross-linking by a targeted anthraquinone derivative of the invention.

FIG. 12 is a PAGE autoradiogram illustrating various aspects of the relative activity of the two moieties: 1,4-dimethylanthraquinone (Me$_2$AQ) and anthraquinone itself (AQ).

Lanes 1–3 show the effect of increasing duration of irradiation on the formation of cross-linked product between the targeted anthraquinone derivative D-Me$_2$AQ and a target strand TCAG (SEQ ID NO:4). TCAG (SEQ ID NO:4) was present in the reaction mixture at a concentration of 10 mM, and D-Me$_2$AQ was present at a concentration of 100 mM. Irradiation times for lanes 1, 2, and 3 are 0, 30 and 120 minutes, respectively, and an increasing amount of cross-linked product is evident.

Lanes 14–19 illustrate the lack of activity exhibited by D-AQ under various reaction conditions. The reactant concentrations for each lane are shown in Table 2 below. Note that the lanes are paired, showing the results of 30 minute and 120 minute irradiations for even-numbered and odd-numbered lanes, respectively.

TABLE 2

| LANES | [TCAG(SEQ ID NO:4)] | [D-AO] |
| --- | --- | --- |
| 4–5 | 2.2 µM | 2.2 µM |
| 6–7 | 220 nM | " |
| 8–9 | 20 nM | " |
| 10–11 | 1 µM | 1 µM |
| 12–13 | 100 nM | " |
| 14–15 | 10 nM | " |
| 16–17 | 100 nM | 100 nM |
| 18–19 | 10 nM | " |

EXAMPLE 11

Figure 13:
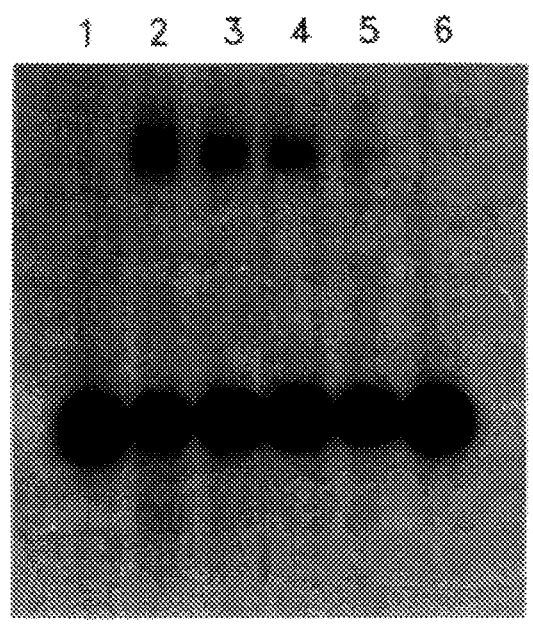
FIG. 13 is an autoradiogram of a denaturing polyacrylamide gel illustrating the quenching effect of a nucleophile on an irradiation-induced cross-linking of an oligodeoxynucleotide target molecule by a targeted anthraquinone derivative of the invention.

Quenching of cross-linking reaction by nucleophile. D-Me$_2$AQ (50 nM) was irradiated with target strand, TCAG (SEQ ID NO:4) (10 nM), under standard conditions in the presence of a nucleophile, aniline (neutralized to pH 7). The concentration of aniline was varied to demonstrate the quenching effect of a nucleophile on the alkylation of a target oligonucleotide by D-Me$_2$AQ. FIG. 13 is a PAGE autoradiogram illustrating the results of this aspect of the alkylation reaction. Lane 1 shows a mixture of D-Me$_2$AQ (50 nM) and a target strand TCAG (SEQ ID NO:4) (10 nM) with no irradiation. Lane 2 shows a similar reaction mixture that was irradiated for 30 minutes. Lanes 3–5 show similar reaction mixtures, also irradiated for 30 minutes, but having added aniline of 100 µM, 1 mM, and 5 mM, respectively. Lane 6 shows an irradiated (30 minutes) reaction mixture of donor strand (without Me₂AQ) and TCAG (SEQ ID NO:4).

FIG. 13 illustrates the direct relationship between the quenching of the photolytically induced crosslinking by Me₂AQ and the concentration of aniline in the reaction mixture. The strong nucleophilic activity of aniline apparently interferes with the reaction between Me₂AQ and the nucleophilic bases of DNA.

EXAMPLE 12

It is believed that Me₂AQ effectively alkylates DNA in part because the Me₂AQ moiety intercalates into the DNA helix. If this is the case, then presumably the Me₂AQ intercalation would be observed as a stabilization of the reversible hybridization of target and donor strands.

The thermal stability (i.e., resistance to thermal denaturation) of various combinations of the donor strand (D (SEQ ID NO:1)), the targeted AQ derivative (D-Me₂AQ), the untargeted AQ derivative (Me₂AQ), with the donor strand (SEQ ID NO:1) were hydridized with the target strand (TCAG (SEQ ID NO:4)). In each hybridization the reactants were included in the following proportions:

Donor: 2.2 µM Donor strand (SEQ ID NO:1)+2.2 µM TCAG (SEQ ID NO:4)

D+Me₂AQ: 2.2 µM Donor strand (SEQ ID NO:1)+2.2 µM TCAG (SEQ ID NO:4)
2.2 µM Me₂AQ D-Me₂AQ: 2.2 µM D-Me₂AQ+2.2 µM TCAG (SEQ ID NO:4)

Figure 14:
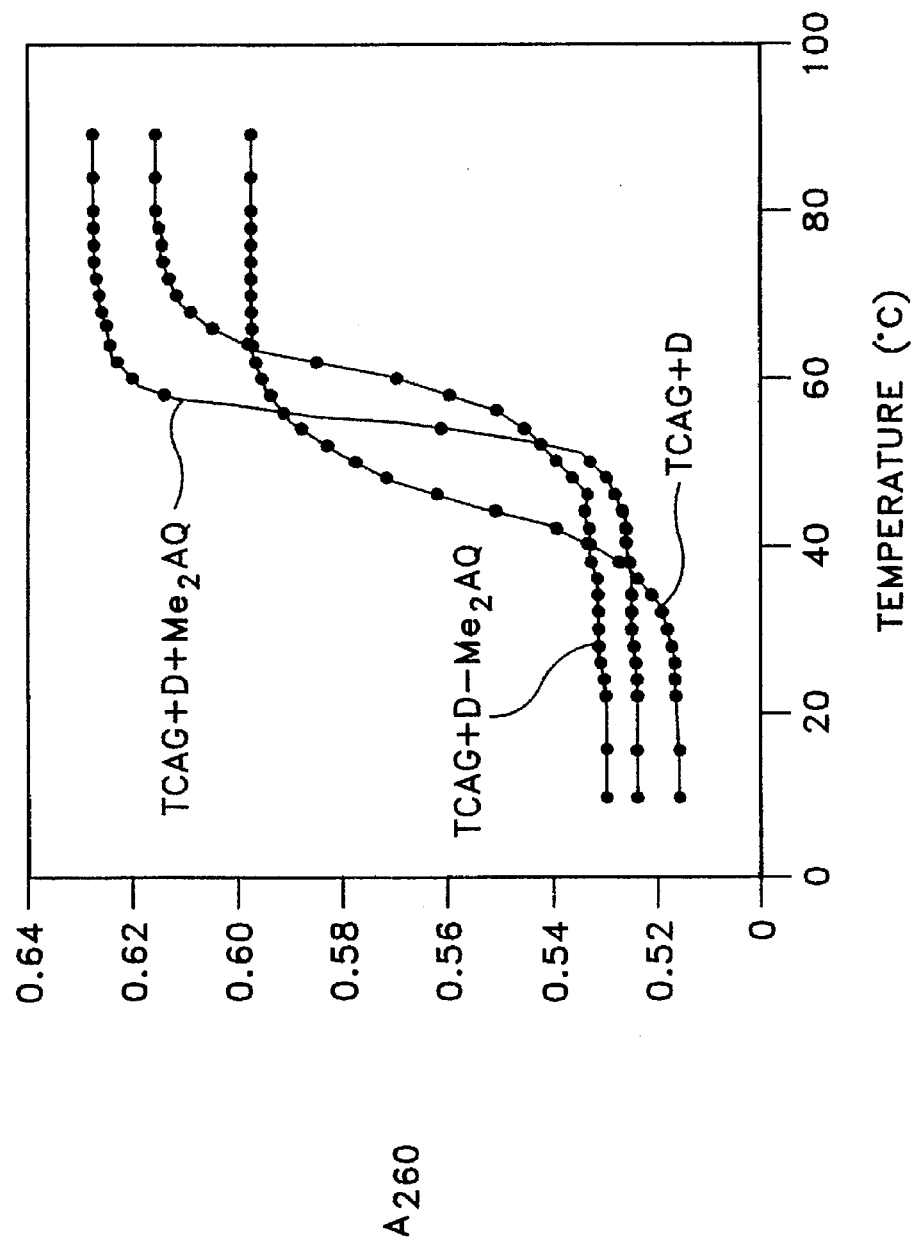
FIG. 14 is a graph illustrating the temperature stability of annealed complexes of an oligodeoxynucleotide target molecule and a targeted anthraquinone derivative of the invention.

The hybridizations were performed in reaction volumes of 1 mL in 10 mM phosphate buffer (pH 7) and 100 mM NaCl. The reaction mixtures were then heated to 80° C. and slowly cooled to 10° C over four hours. The melting temperatures ($T_m$) of the duplexes were determined by plotting the increases in $A_{260}$ against temperature. The results are shown in FIG. 14.

The $T_m$ of TCAG (SEQ ID NO:4) hybridized with the donor strand D (SEQ ID NO:1) was found to be 47° C. Me₂AQ was observed to increase the $T_m$ of hybridization. When untargeted Me₂AQ was mixed with the donor strand D (SEQ ID NO:1) and the target strand TCAG (SEQ ID NO:4), the $T_m$ Of the system was 54° C. Greatest stability enhancement was observed when the targeted AQ derivative D-Me₂AQ was mixed with TCAG (SEQ ID NO:4). In this case, the $T_m$ was 57° C. As a result, it is believed that Me₂AQ does intercalate into DNA, thereby stabilizing duplex DNA structures.

EXAMPLE 13

Mono dimethoxytrityl ether of 2-(N,N-diethanolamino)-1,4-dimethylanthraquinone. A mixture of 2-chloro-1,4-dimethylanthraquinone (10 mmole) and an excess (3.8 mL; 40 mmole) of diethanolamine in DMSO (20 mL) is heated to 150° C. After 24 hours, the reaction mixture is cooled to room temperature, then poured into water (70 mL). The red precipitate is filtered off, washed thoroughly with water, and dried under vacuum. The crude product is used without further purification.

The crude compound is dissolved in pyridine (20 mL) and triethyl amine (1.7 mL), cooled to 0° C., followed by the addition of 4-dimethylaminopyridine (DMAP) (0.2 g) and 4,4'-dimethoxytrityl chloride (DMT-Cl) (4.0 g; 12 mmol). The reaction mixture is warmed to room temperature. After 4 hours of reaction, more DMT-Cl (1 g; 3 mmol) is added to the reaction mixture and reacted one more hour, then concentrated to dryness. The residue is then partitioned between methylene chloride and saturated sodium bicarbonate solution. The organic solution is separated and dried, purified by flash column chromatography on silica gel, eluted with 1% Et₃N/1% CH₃OH/CH₂Cl₂ to afford the product; mono-DMT-protected 2-(N,N-diethanolamino)-1,4-dimethylanthraquinone.

The mono dimethoxytrityl ether of 2-(N,N-dihexanolamino) 1,4-dimethylanthraquinone is prepared by same method as the N,N-diethanolamino compound.

Phosphorylation of mono-DMT-protected dimethyl anthraquinone pseudonucleosides. A methylene chloride solution (8 mL) of the mono dimethoxytrityl ether of2-(N, N-diethanolamino)-1,4-dimethyl anthraquinone, (0.39 mmol) is prepared and held at 0° C. To this solution are added pyridine (0.1 mL) and a 1M solution of 2-chloro-4H-1,2,3-benzodioxaphosphorin-4-one in methylene chloride (1.17 mL; 1.17 mmol). After 0.5 hours of reaction at 0° C., the reaction mixture is washed with 1M triethyl ammonium bicarbonate (TEAB) aqueous solution. The organic solution is separated, dried over Na₂SO₄, and purified by flash column chromatography, eluted with 1.5% Et₃N/5% CH₃OH/CH₂Cl₂. Fractions of the product are combined, washed with 1M TEAB aqueous solution, dried over Na₂SO₄, and concentrated, affording phosphorylated DMT-protected dimethylanthraquinone. This compound behaves like conventional nucleosides for purposes of DNA synthesis and so may be called a "pseudonucleoside". As a result, the DMT-protected dimethyl anthraquinone is then capable of being incorporated at any position in a synthetic oligonucleotide.

EXAMPLE 14

Preparation of a dimethylanthraquinone-piperazinyl derivative. A mixture of 2-chloro-1,4-dimethylanthraquinone (1 g) and 1-(2-hydroxyethyl) piperazine (5 g) is heated at 150° C. for 30 min. After cooling to room temperature, water is added, and the material is filtered. Recrystallization from chloroform yields 1-[1-(2-hydroxyethyl)piperazinyl]-1,4-dimethylanthraquinone.

Synthesis of dimethylanthraquinone-piperazinyl phosphoramidite. 1-(1-[2-hydroxyethyl)piperazinyl-1,4-dimethylanthraquinone (1 mmol) is dissolved in CH₂Cl₂ (2 mL), and N-ethyldiisopropylamine (760 µL, 4 mmol) and N,N-diisopropylmethylphosphonamidic chloride (194 µL, 1 mmol) are added. After 30 min., the solution is poured into ethylacetate ( 5 mL, previously washed with 2×5 mL of 5% NaHCO₃, and 2×5 mL of saturated NaCl). The ethylacetate phase is dried over Na₂SO₄ and evaporated to an oil, N-1,4-dimethylanthraquinonyl-O-methoxydiisopropylamino phosphite 1-(2-hydroxyethyl) piperazine.

Preparation of dimethylanthraquinone methylene-linked phosphoramidite. Preparation of the methylene-linked dimethylanthraquinone phosphoramidite is accomplished as described above, but with substitution of hexanolamine for the 1-(2-hydroxyethyl)piperazine.

Synthesis of dimethylanthraquinone-linked oligodeoxynucleotides. Without further purification, the dimethylanthraquinone-linked phosphoramidites are dissolved in the appropriate amount of acetonitrile and used directly in oligonucleotide preparation.

Thus, while we have described what are presently the preferred embodiments of the present invention, other and further changes and modifications could be made without departing from the scope of the invention, and it is intended by the inventors to claim all such changes and modifications.

We claim:

1. A targeted anthraquinone derivative for alkylating a target molecule, said anthraquinone derivative having the molecular formula:

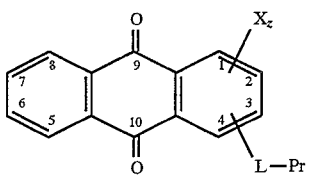

wherein L is a linking group for attaching a probe through other than a nitrogen atom at one of carbon atoms 1–8 of the anthraquinone compound; Pr is a probe that includes a localizing moiety that preferentially localizes to a nucleic acid target molecule; wherein X is an inducible reactive moiety selected from the group consisting of —$CH_3$ and —$CH_2Y$, wherein Y is a displaceable moiety; z is an integer from 1 to 7, and said z number of X groups are attached at any of carbon atoms 1–8 of the anthraquinone compound.

2. The targeted anthraquinone derivative of claim 1, wherein said X groups are methyl groups, z is an integer from 1 to 4, said z number of methyl groups are attached at any of carbon atoms 1, 4, 5, 8 of the anthraquinone compound; and
    wherein said anthraquinone derivative can alkylate said target molecule after photochemical activation by light irradiation.

3. The targeted anthraquinone derivative of claim 1, wherein said X groups have the general molecular formula —$CH_2$—Y, and, for each —$CH_2$—Y, group Y is a displaceable moiety independently selected from the group consisting of —Br, —Cl, —F, —I, —OAc, —OH, —$OSO_2CH_3$, —$OSO_2C_6H_4CH_3$, —$OCH_2CH_3$, —$OCONHCH_3$, and —$OCONHCH_2CH_2Cl$; and
    wherein said targeted anthraquinone derivative can alkylate said target molecule after activation via chemical or enzymatic reduction to produce an electrophilic species.

4. The targeted anthraquinone derivative of claim 1, comprising a bifunctional anthraquinone compound having the general molecular formula:

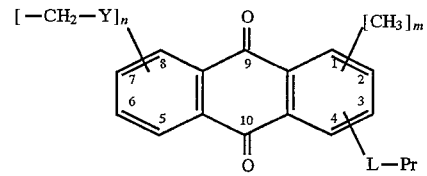

wherein m is an integer from 1 to 4, and said m number of methyl groups are attached at any of carbon atoms 1, 4, 5, 8 of said anthraquinone compound;
    wherein n is an integer from 1 to 6, said n number of —$CH_2$—Y groups are attached at any of carbon atoms 1–8 of said anthraquinone compound, Y is a displaceable moiety, and, for each —$CH_2$—Y, Y is independently selected from the group consisting of —Br, —Cl, —F, —I, —OAc, —OH, —$OSO_2CH_3$, —$OSO_2C_6H_4CH_3$, —$OCH_2CH_3$, —$OCONHCH_3$, and —$OCONHCH_2CH_2Cl$;
    wherein said anthraquinone derivative can alkylate said target molecule through said methyl groups after photochemical activation by light irradiation; and
    wherein said anthraquinone derivative can alkylate said target molecule through said —$CH_2$—Y groups after activation via chemical or enzymatic reduction to produce an electrophilic species.

5. The targeted anthraquinone derivative of claim 1, wherein L comprises a chain —$R_1$—$R_2$—$R_3$—, in which $R_1$ is selected from the group consisting of —$CH_2$—$CH_2$— CO—NH—, —S—, —O—, and —$CH_2$—, in which $R_2$ comprises a stable spacer group between $R_1$ and $R_3$, and in which $R_3$ is selected from the group consisting of —$NH_2$, —SH, —OH, and COOH.

6. The targeted anthraquinone derivative of claim 5, wherein said L is selected from the group consisting of alkanol amines and hydroxyalkyl piperazines.

7. The targeted anthraquinone derivative of claim 6, wherein said L is hexanolamine.

8. The targeted anthraquinone derivative of claim 1, wherein said probe Pr is an oligonucleotide.

9. The targeted anthraquinone derivative of claim 8, wherein said probe Pr is a DNA strand.

10. The targeted anthraquinone derivative of claim 8, wherein said probe Pr is an RNA strand.

11. The targeted anthraquinone derivative of claim 8, wherein said anthraquinone compound is attached at a terminal position on said oligonucleotide.

12. The targeted anthraquinone derivative of claim 8, wherein said anthraquinone compound is attached at an intermediate position on said oligonucleotide.

13. The targeted anthraquinone derivative of claim 8 wherein said oligonucleotide is modified for in vivo use by means of including nuclease-resistant nucleotide analogs or attachment of moieties allowing traversal of cell membranes.

14. The targeted anthraquinone derivative of claim 13, wherein said oligonucleotide has a modified phosphoribose backbone.

15. The targeted anthraquinone derivative of claim 13, wherein said oligonucleotide has a modified base.

16. The targeted anthraquinone derivative of claim 1, having the molecular formula:

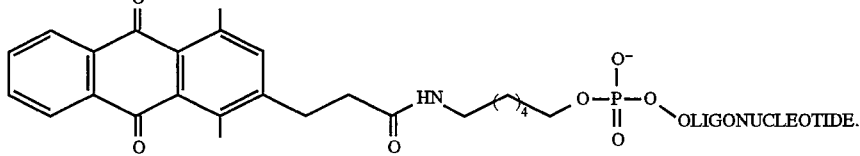

17. A process for selectively alkylating a target molecule, comprising the steps of:
 a) providing an anthraquinone derivative capable of alkylating a target molecule;
 b) introducing the anthraquinone derivative into an in vitro system containing a target molecule; and
 c) activating the anthraquinone derivative thereby causing alkylation of the target molecule by the anthraquinone derivative;
wherein said providing step further comprises providing as said anthraquinone derivative an anthraquinone compound having the general molecular formula:

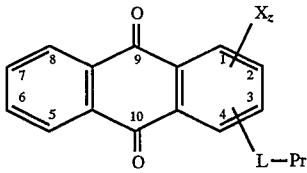

wherein L is a linking group for attaching to a probe and L is attached by other than a nitrogen atom at one of carbon atoms 1–8; wherein Pr is a probe that includes a localizing moiety that preferentially localizes to a nucleic acid target molecule; wherein X is an inducible reactive moiety selected from the group consisting of —CH₃ and —CH₂Y, wherein Y is a displaceable moiety; z is an integer from 1 to 7, and said z number of X groups are attached at any of carbon atoms 1–8 of the anthraquinone compound.

18. The process of claim 17, wherein said providing step further comprises providing an anthraquinone compound wherein the X groups are methyl groups, z is an integer from 1 to 4, and said z number of methyl groups are located at any of carbon atoms 1, 4, 5, 8 of the anthraquinone compound; and
 wherein said activating step further comprises photochemically activating said anthraquinone derivative by light irradiation.

19. The process of claim 17, wherein said providing step further comprises providing an anthraquinone compound wherein said X groups have the general molecular formula —CH₂—Y, and, for each —CH₂—Y group, Y is a displaceable moiety independently selected from the group consisting of —Br, —Cl, —F, —I, —OAc, —OH, —OSO₂CH₃, —OSO₂C₆H₄CH₃, —OCH₂CH₃, —OCONHCH₃, and —OCONHCH₂CH₂Cl; and
 wherein said activating step further comprises activating said anthraquinone derivative via chemical or enzymatic reduction to produce an electrophilic species.

20. The process of claim 17, wherein said providing step further comprises providing an anthraquinone compound having the general molecular formula:

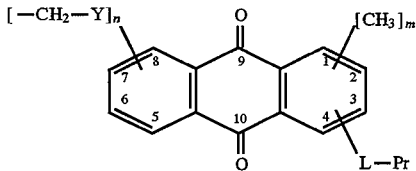

wherein m is an integer from 1 to 4, and said m number of methyl groups are attached at any of carbon atoms 1, 4, 5, 8 of said anthraquinone compound;
 wherein n is an integer from 1 to 6, said n number of —CH₂—Y groups are attached at any of carbon atoms 1–8 of said anthraquinone compound, Y is a displaceable moiety, and, for each —CH₂—Y group, Y is independently selected from the group consisting of —Br, —Cl, —F, —I, —OAc, —OH, —OSO₂CH₃, —OSO₂C₆H₄CH₃, —OCH₂CH₃, —OCONHCH₃, and —OCONHCH₂CH₂Cl; and
 wherein said activating step further comprises activating said methyl groups by light irradiation and/or activating said —CH₂—Y groups via chemical or enzymatic reduction to produce an electrophilic species.

21. The process of claim 17, further comprising selecting as said L group a group comprising a chain —R₁—R₂—R₃—, in which R₁ is selected from the group consisting of —CH₂—CH₂—CO—NH—, —S—, —O—, and —CH₂—, in which R₂ comprises a stable spacer group between R₁ and R₃, and in which R₃ is selected from the group consisting of —NH₂, —SH, —OH, and COOH.

22. The process of claim 21, further comprising selecting as said L group a compound selected from the group consisting of alkanol amines and hydroxyalkyl piperazines.

23. The process of claim 22, further comprising selecting hexanolamine as said L group.

24. The process of claim 17 further comprising selecting an oligonucleotide as said probe.

25. The process of claim 24, further comprising selecting a DNA strand as said oligonucleotide.

26. The process of claim 24, further comprising selecting an RNA strand as said oligonucleotide.

27. The process of claim 24, further comprising providing as said anthraquinone derivative an anthraquinone compound attached at a terminal position on said oligonucleotide.

28. The process of claim 24, further comprising providing as said anthraquinone derivative an anthraquinone compound attached at an intermediate position on said oligonucleotide.

29. The process of claim 24, further comprising selecting an oligonucleotide that has been modified for in vivo use as said probe by including nuclease-resistant nucleotide analogs or by attachment of moieties allowing traversal of cell membranes.

30. The process of claim 29, further comprising selecting a modified oligonucleotide having a modified phosphoribose backbone as said oligonucleotide.

31. The process of claim 29, further comprising selecting a modified oligonucleotide having at least one modified base as said oligonucleotide.

32. The process of claim 17, wherein said providing step further comprises providing an anthraquinone compound having the general molecular formula:

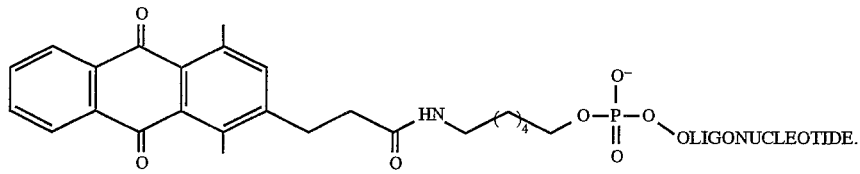

UNITED STATES PATENT AND TRADEMARK OFFICE
CERTIFICATE OF CORRECTION

PATENT NO. : 5,650,399  
DATED : July 22, 1997  
INVENTOR(S) : Rokita et al.

Page 1 of 4

It is certified that error appears in the above-indentified patent and that said Letters Patent is hereby corrected as shown below:

In Column 3, Line 5,      the patent now reads "1-methylanthratquinone"; this should read -- 1-methylanthraquinone --.

In Column 6, Line 19,      the patent now reads "NH, S, -Nh-, -S-, -Cl$_2$-, -CH$_2$-, -O- and COOH-."; this should read -- -NH-, -S-, -CH$_2$-, -O-, and -COO- --.

In Column 9, Line 43,      the patent now reads "from i to 4 methyl"; this should read -- from 1 to 4 methyl --.

In Column 10, Line 14,      the patent now reads "NH, S, -Nh-, -S-, -CH$_2$-, -O-, -COO- and COO"; this should read -- -NH-, -S-, -CH$_2$-, -O-, and -COO- --.

UNITED STATES PATENT AND TRADEMARK OFFICE
CERTIFICATE OF CORRECTION

PATENT NO. : 5,650,399
DATED : July 22, 1997
INVENTOR(S) : Rokita et al.

It is certified that error appears in the above-indentified patent and that said Letters Patent is hereby corrected as shown below:

In Column 11, Line 13,   the patent now reads "X is an Inducible reactive moiety as according to the process of the invention"; this should read --X is an inducible reactive moiety as described above for the targeted anthraquinone derivitives useful according to the process of the invention--.

In Column 12, Line 14,   the patent now reads "Chemistry, 1, 1-12"; this should read --Chemistry, 2, 1-12--.

In Column 12, Line 26,   the patent now reads "Res., 55, 4513"; this should read --Res., 15, 4513--.

In Column 16, Line 46,   the patent now reads "1.37 mole)"; this should read --1.37 mmole)--.

In Column 20 Line 24,   the patent now reads "TCTAAG. The"; this should read --TCTAAG (SEQ ID NO: 2). The--.

In Column 22, Line 2,   the patent now reads "Lane 7: i M piperidine"; this should read --Lane 7: 1 M piperidine--.

UNITED STATES PATENT AND TRADEMARK OFFICE
CERTIFICATE OF CORRECTION

PATENT NO. : 5,650,399
DATED : July 22, 1997
INVENTOR(S) : Rokita et al.

It is certified that error appears in the above-indentified patent and that said Letters Patent is hereby corrected as shown below:

In Column 23, Line 22,   the patent now reads "D-Me$_2$AP: TCAG"; this should read --D-Me$_2$Q: TCAG--.

In Column 23, Line 23,   the patent now reads "and donor:TTAG mixtures"; this should read --D-Me$_2$AQ:TTAG (SEQ ID NO:6) mixtures--.

In Column 23, Line 24,   the patent now reads "D-Me$_2$AP:TAAG"; this should read --D-Me$_2$AQ:TAAG--.

In Column 23, Line 26,   the patent now reads "and donor: D-Me$_2$AQ:TGAG"; this should read --and D-Me$_2$AQ:TGAG--.

In Column 24, Line 48,   the patent now reads "Soc. Jpn., 21, 3121"; this should read --Soc. Jpn., 61, 3121--.

In Column 25, Line 45,   the patent now reads "Anthraqulnonyl-3"; this should read --Anthraquinonyl-3--.

In Column 25, Line 56,   the patent now reads "8.n (1H, s),"; this should read --8.11 (1H, s),--.

UNITED STATES PATENT AND TRADEMARK OFFICE
CERTIFICATE OF CORRECTION

PATENT NO. : 5,650,399
DATED : July 22, 1997
INVENTOR(S) : Rokita et al.

It is certified that error appears in the above-indentified patent and that said Letters Patent is hereby corrected as shown below:

In Column 26, Line 33,     the patent now reads "10 mM"; this should read --10 nM--.

In Column 26, Line 34,     the patent now reads "100 mM"; this should read --100 nM--.

In Table 2, Line 45,       the patent now reads "[D-AO]"; this should read --[D-AQ]--.

In Column 27, Line 46,     the patent now reads "$T_m$ Of the system"; this should read --$T_m$ of the system--.

Signed and Sealed this

Eighteenth Day of November 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

ACGTCAGGTG GCACT                                      15

( 2 ) INFORMATION FOR SEQ ID NO:2:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

AGTGCCACCT GACGTCTAAG                              20

( 2 ) INFORMATION FOR SEQ ID NO:3:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

AGTGCCACCT GACGTAAG                                 18

( 2 ) INFORMATION FOR SEQ ID NO:4:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

AGTGCCACCT GACGTCAG                                 18

( 2 ) INFORMATION FOR SEQ ID NO:5:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear

```
    ( i i ) MOLECULE TYPE: DNA ( x i ) SEQUENCE DESCRIPTION: SEQ ID NO:5:

AGTGCCACCT GACGTGAG                                                    1 8

( 2 ) INFORMATION FOR SEQ ID NO:6:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

AGTGCCACCT GACGTTAG                                                    1 8
```